United States Patent [19]

Biggadike et al.

[11] Patent Number: 6,013,244
[45] Date of Patent: Jan. 11, 2000

[54] 21-(2-OXO-TETRAHYDROFURAN)-THIO PREGNANE DERIVATIVES, A PROCESS FOR THEIR PRODUCTION AND PHARMACEUTICAL COMPOSITIONS CONTAINING THEM

[75] Inventors: Keith Biggadike; Rosanne Mary Farrell, both of Stevenage, United Kingdom

[73] Assignee: Glaxo Wellcome Inc., Research Triangle Park, N.C.

[21] Appl. No.: 09/091,749

[22] PCT Filed: Dec. 19, 1996

[86] PCT No.: PCT/GB96/03153

§ 371 Date: Jun. 24, 1998

§ 102(e) Date: Jun. 24, 1998

[87] PCT Pub. No.: WO97/24367

PCT Pub. Date: Jul. 10, 1997

[30] Foreign Application Priority Data

Dec. 29, 1995 [GB] United Kingdom .................. 9526630
Jun. 21, 1996 [GB] United Kingdom .................. 9613036

[51] Int. Cl.[7] .............................. A61K 31/34; A61L 9/04; C07D 307/18
[52] U.S. Cl. ............................ 424/45; 514/473; 514/887; 514/465; 549/314; 549/435; 424/434
[58] Field of Search .................................... 514/465, 473, 514/887; 549/314, 435; 424/45, 434

[56] References Cited

PUBLICATIONS

Chemical & Pharmaceutical Bulletin, 37(12), Dec. 1989, Japan pp. 3286–3293 XP002026042 Mitsukuchi et al.
Chemical & Pharmaceutical Bulletin, 37 (7), Jul. 1989, Japan pp. 1795–1801 XP002026043 Mitsukuchi et al.

*Primary Examiner*—Joseph K. McKane
*Assistant Examiner*—Taofiq A. Solola
*Attorney, Agent, or Firm*—Nixon & Vanderhye

[57] ABSTRACT

Compounds of the pregnane series are described having general formula (I) or their solvates in which $R_1$ individually represents —OC(=O)$C_{1-6}$ alkyl; $R_2$ individually represents hydrogen, methyl (which may be in the α or β configuration) or methylene; or $R_1$ and $R_2$ together represent formula (a) where $R_5$ and $R_6$ are the same or different and each represents hydrogen or $C_{1-6}$ alkyl; $R_3$ and $R_4$ are the same or different and each represents hydrogen or halogen; and === represents a single or a double bond. Compounds of formula (I) and their solvates are useful as anti-inflammatory or anti-allergic agents.

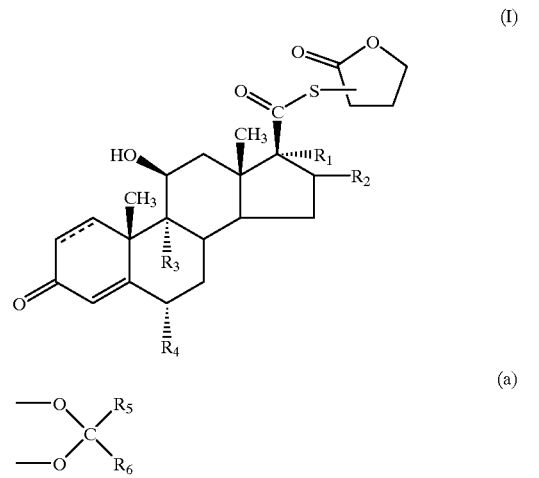

32 Claims, No Drawings

21-(2-OXO-TETRAHYDROFURAN)-THIO PREGNANE DERIVATIVES, A PROCESS FOR THEIR PRODUCTION AND PHARMACEUTICAL COMPOSITIONS CONTAINING THEM

This application is a 371 of PCT/GB96/03153 filed Dec. 19, 1996.

The present invention relates to novel anti-inflammatory and anti-allergic compounds of the pregnane series and to processes for their preparation. The present invention also relates to pharmaceutical formulations containing the compounds and to therapeutic uses thereof, particularly for the treatment of inflammatory and allergic conditions.

Glucocorticosteroids which have anti-inflammatory properties are known and are widely used for the treatment of inflammatory disorders or diseases such as asthma and rhinitis. However, such glucocorticosteroids may suffer from the disadvantage of causing unwanted systemic effects following administration. WO94/13690, WO94/14834, WO92/13873 and WO92/13872 all disclose glucocorticosteriods which are alleged to possess anti-inflammatory activity coupled with reduced systemic potency.

The present invention provides a novel group of compounds which possess useful anti-inflammatory activity whilst having little or no systemic activity. Thus, the compounds of the present invention represent a safer alternative to those known glucocorticoids which have poor side-effect profiles.

Thus, according to one aspect of the invention, there is provided a compound of formula (I)

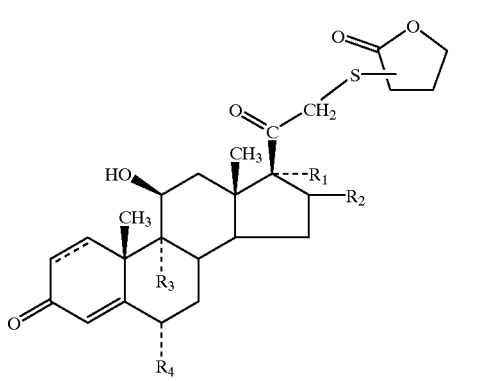

(I)

and solvates thereof, in which $R_1$ individually represents —OC(=O)$C_{1-6}$ alkyl;

$R_2$ individually represents hydrogen, methyl (which may be in the α or β configuration) or methylene;

or $R_1$ and $R_2$ together represent

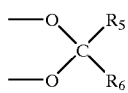

wherein $R_5$ and $R_6$ are the same or different and each represents hydrogen or $C_{1-6}$ alkyl;

$R_3$ and $R_4$ are the same or different and each represents hydrogen or halogen; and ═ represents a single or a double bond.

In the above definitions, the term "alkyl" as a group or part of a group means a straight chain, or, where available, a branched chain alkyl moiety. For example, it may represent a $C_{1-4}$ alkyl function as represented by methyl, ethyl, n-propyl, i-propyl, n-butyl and t-butyl.

The solvates may, for example, be hydrates.

References hereinafter to a compound according to the invention includes both compounds of formula (I) and their solvates, particularly pharmaceutically acceptable solvates.

It will be appreciated that the invention includes within its scope all stereoisomers of the compounds of formula (I) and mixtures thereof.

In particular the compounds of formula (I) contain an asymmetric centre at the point of attachment of the lactone moiety. Thus, the invention includes within its scope both of the diastereoisomers at this asymmetric centre and mixtures thereof.

Diastereoisomers and mixtures thereof at the asymmetric centre formed when $R_1$ and $R_2$ together represents

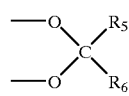

and $R_5$ and $R_6$ are different are also included within the scope of the present invention.

The sulphur linkage to the lactone moiety can be to either the alpha, beta or gamma carbon atoms of the lactone,

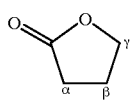

A preferred group of compounds of the invention are compounds of formula (I) in which $R_1$ individually represents OC(=O)$C_{1-6}$ alkyl, more preferably OC(=O)$C_{1-3}$ alkyl, especially OC(=O)ethyl. Compounds within this group in which $R_2$ is methyl are generally preferred.

Another preferred group of compounds are compounds of formula (I) in which $R_1$ and $R_2$ together represent

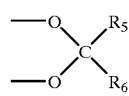

wherein $R_5$ and $R_6$ are the same or different and each represents hydrogen or $C_{1-6}$ alkyl, particularly hydrogen or $C_{1-3}$ alkyl, especially hydrogen, methyl or n-propyl.

Compounds of formula (I) in which $R_3$ and $R_4$, which can be the same or different, each represents hydrogen, fluorine or chlorine, particularly hydrogen or fluorine, are preferred. Especially preferred are compounds in which both $R_3$ and $R_4$ are fluorine.

A particularly preferred group of compounds of the present invention are compounds of formula (I) in which $R_1$ is OC(=O)$C_{1-6}$ alkyl, particularly OC(=O)$C_{1-3}$ alkyl, especially OC(=O)ethyl; $R_2$ is methyl; $R_3$ and $R_4$, which can be the same or different, each represents hydrogen or fluorine, especially fluorine; and ═ represents a single or a double bond.

A further particularly preferred group of compounds of the invention are compounds of formula (I) in which $R_1$ and $R_2$ together represent

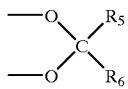

wherein $R_5$ and $R_6$ are the same or different and each represents hydrogen or $C_{1-6}$ alkyl, particularly hydrogen or $C_{1-3}$ alkyl, especially hydrogen, methyl or n-propyl; $R_3$ and $R_4$ which can be the same or different each represents hydrogen or fluorine, especially fluorine; and ═ represents a single or a double bond. The R-isomers of compounds within this group in which $R_5$ and $R_6$ are different are preferred.

It is to be understood that the present invention covers all combinations of particularly and preferred groups referred to hereinabove.

Compounds of formula (I) include:

6α,9α-Difluoro-11β-hydroxy-16α-methyl-21-(2-oxo-tetrahydro-furan-3-yl-sulfanyl)-17α-propionyloxy-pregn-4-ene-3,20-dione;

16α,17α-(R-Butylidenedioxy)-6α,9α-difluoro-11β-hydroxy-21-(2-oxo-tetrahydro-furan-3-yl-sulfanyl)-pregna-1,4-diene-3,20-dione;

16α,17α-Butylidenedioxy-11β-hydroxy-21-(2-oxo-tetrahydrofuran-3-yl-sulfanyl)-pregna-1,4-diene-3,20-dione;

6α,9α-Difluoro-11β-hydroxy-16α,17α-isopropylidenedioxy-21-(2-oxo-tetrahydro-furan-5-yl-sulfanyl)-pregna-1,4-diene-3,20-dione;

9α-Fluoro-11β-hydroxy-16α,17α-isopropylidenedioxy-21-(2-oxo-tetrahydro-furan-3-yl-sulfanyl)-pregna-1,4-diene-3,20-dione;

9α-Fluoro-11β-hydroxy-16β-methyl-21-(2-oxo-tetrahydro-furan-3-yl-sulfanyl)-17α-propionyloxy-pregna-1,4-diene-3,20-dione;

and solvates thereof.

Preferred compounds of formula (I) include;

6α,9α-Difluoro-11β-hydroxy-16α-methyl-21-(2-oxo-tetrahydro-furan-3-yl-sulfanyl)-17α-propionyloxy-pregna-1,4-diene-3,20-dione;

6α,9α-Difluoro-11β-hydroxy-16α,17α-isopropylidenedioxy-21-(2-oxo-tetrahydro-furan-3-yl-sulfanyl)-pregna-1,4-diene-3,20-dione;

6α,9α-Difluoro-11β-hydroxy-16α,17α-isopropylidenedioxy-21-(2-oxo-tetrahydro-furan-3-yl-sulfanyl)-pregn-4-ene-3,20-dione;

6α,9α-Difluoro-11β-hydroxy-16α,17α-isopropylidenedioxy-21-(2-oxo-tetrahydro-furan4-yl-sulfanyl)-pregna-1,4-diene-3,20-dione;

16α,17α-(R-Butylidenedioxy)-6α,9α-difluoro-11β-hydroxy-21-(2-oxo-tetrahydro-furan4-yl-sulfanyl)-pregn-4-ene-3,20-dione;

16α,17α-(R-Butylidenedioxy)-6α,9α-difluoro-11β-hydroxy-21-(2-oxo-tetrahydro-furan-3-yl-sulfanyl)-pregn-4-ene-3,20-dione;

and solvates thereof.

It will be appreciated that each of the above compounds of formula (I) includes the individual R and S diastereoisomers at the asymmetric centre at the point of attachment of the lactone moiety as well as mixtures thereof. It will further be appreciated that the compounds of formula (I) may include the individual R and S diastereoisomers at the asymmetric centre formed when $R_1$ and $R_2$ together represent

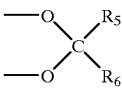

wherein $R_1$ and $R_2$ are different, and mixtures thereof. Thus, the individual R and S diastereoisomers isolated such as to be substantially free of the other diastereoisomer ie pure and mixtures thereof are included within the scope of the present invention. An individual R or S diastereoisomer isolated such as to be substantially free of the other diastereoisomer ie pure will be isolated such that less than 10%, preferably less than 1% e.g. less than 0.1% of the other diastereoisomer is present.

The compounds of formula (I) have potentially beneficial anti-inflammatory or anti-allergic effects, particularly upon topical administration, demonstrated by, for example, their ability to bind to the glucocorticoid receptor and to illicit a response via that receptor. Hence, the compounds of formula (I) are useful in the treatment of inflammatory and/or allergic disorders. Further the compounds of formula (I) possess the advantage of having little or no systemic activity. Therefore, the compounds of the invention may represent a safer alternative to those known anti-inflammatory glucocorticoids which have poor side effect profiles.

Examples of disease states in which the compounds of the invention have utility include skin diseases such as eczema, psoriasis, allergic dermatitis neurodermatitis, pruritis and hypersensitivity reactions: inflammatory conditions of the nose, throat or lungs such as asthma (including allergen-induced asthmatic reactions), rhinitis (including hayfever). nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

Compounds of the invention may also have use in the treatment of conjunctiva and conjunctivitis.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory and anti-allergic agents.

There is thus provided as a further aspect of the invention a compound of formula (I) or a physiologically acceptable solvate thereof for use in human or veterinary medicine, particularly in the treatment of patients with inflammatory and/or allergic conditions.

According to another aspect of the invention, there is provided the use of a compound of formula (I) or physiologically acceptable solvate thereof for the manufacture of a medicament for the treatment of patients with inflammatory and/or allergic conditions.

In a further or alternative aspect, there is provided a method for the treatment of a human or animal subject with an inflammatory and/or allergic condition, which method comprises administering to said human or animal subject an effective amount of a compound of formula (I) or physiologically acceptable solvate thereof.

The compounds according to the invention may be formulated for administration in any convenient way, and the invention therefore also includes within its scope pharmaceutical compositions, comprising a compound of formula (I) or physiologically acceptable solvate thereof together, if desirable, in admixture with one or more physiologically acceptable diluents or carriers.

Further, there is provided a process for the preparation of such pharmaceutical compositions which comprises mixing the ingredients.

The compounds according to the invention may, for example, be formulated for oral, buccal, sublingual, parenteral, local or rectal administration, especially local administration.

Local administration as used herein, includes administration by insufflation and inhalation. Examples of various types of preparation for topical administration include ointment, lotions, creams, gels, foams, preparations for delivery by transdermal patches, powders, sprays, aerosols, capsules or cartridges for use in an inhaler or insufflator or drops (e.g. eye or nose drops) solutions/suspensions for nebulisation, suppositories, pessaries, retention enemas and chewable or suckable tablets or pellets (e.g. for the treatment of aphthous ulcers) or liposome or microencapsulation preparations.

Ointments creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquified propellant. Aerosol composition suitable for inhalation can be either a suspension or a solution and generally contain a compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and cosolvents e.g. ethanol.

Advantageously the formulations of the invention may be buffered by the addition of suitable buffering agents.

Capsules and cartridges for use in an inhaler or insufflator, of for example gelatine, may be formulated containing a powder mix for inhalation of a compound of the invention and a suitable powder base such as lactose or starch. Each capsule or cartridge may generally contain between 20 $\mu$g–10 mg of the compound of formula (I). Alternatively, the compounds of the invention may be presented without excipients such as lactose.

The proportion of the active compound of formula (I) in the local compositions according to the invention depends on the precise type of formulation to be prepared but will generally be within the range of from 0.001 to 10.0% by weight. Generally, however for most types of preparations advantageously the proportion used will be within the range of from 0.005 to 1% and preferably 0.01 to 0. 5%. However, in powders for inhalation or insufflation the proportion used will be within the range of from 0.1–2%.

Aerosol formulations are preferably arranged so that each metered dose or "puff" of aerosol contains 20 $\mu$g–2000 $\mu$g, preferably about 20 $\mu$g–500 $\mu$g of a compound of formula (I). Administration may be once daily or several times daily, for example 2, 3, 4 or 8 times, giving for example 1, 2 or 3 doses each time. The overall daily dose with an aerosol will be within the range 100 $\mu$g–10mg preferably, 200 $\mu$g–2000 $\mu$g. The overall daily dose and the metered dose delivered by capsules and cartridges in an inhaler or insufflator will generally be double those with aerosol formulations.

Topical preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrates, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms ie. tablets and capsules. Such dosage unit forms contain from 0.mg to 20 mg preferably from 2.5 to 10 mg of the compounds of the invention.

The compounds according to the invention may in general may be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, e.g. 5–30 mg, dependent on the condition being treated, and the duration of treatment desired.

Slow release or enteric coated formulations may be advantageous, particularly for the treatment of inflammatory bowel disorders.

The pharmaceutical compositions according to the invention may also be used in combination with another therapeutically active agent, for example, a $\beta_2$-adrenoreceptor agonist, an anti-histamine or an antiallergic. The invention thus provides, in a further aspect, a combination comprising a compound of formula (I) or a physiologically acceptable solvate thereof with another therapeutically active agent, for example, a $\beta_2$-adrenoreceptor agonist, an anti-histamine or an anti-allergic.

The combination referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

The compounds of formula (I) and solvates thereof may be prepared by the methodology described hereinafter, constituting a further aspect of this invention.

Thus, according to a first process (A), a compound of formula (I) may be prepared by treating a compound of formula (II)

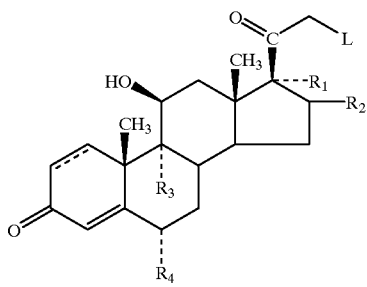
(II)

wherein $R_1$, $R_2$, $R_3$, $R_4$ and ⚌ are as defined hereinbefore for compounds of formula (I) and L represents an appropriate leaving group such as a sulfonate ester e.g. a mesylate, tosylate or triflate, or L represents a halogen such as Cl or Br, with a compound of formula (III)

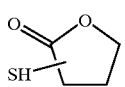
(III)

and salts thereof.

The above alkylation reaction is preferably performed in the presence of a base such as potassium carbonate, sodium hydride or sodium methoxide and in a solvent such as tetrahydrofuran, acetone, dimethylformamide, dimethyl acetamide or dimethylsulphoxide, conveniently at a temperature between about 0° C. to 100° C. and under an inert atmosphere such as nitrogen.

Alternatively, the alkylation reaction may be performed using an organic base such as a tertiary amine, e.g. triethylamine in a solvent such as tetrahydrofuran, dichloromethane or chloroform conveniently at a temperature of between about 0° C. to 100° C. and under an inert atmosphere such as nitrogen.

According to a second process (B), a compound of formula (I) may be prepared by treating a compound of formula (IV)

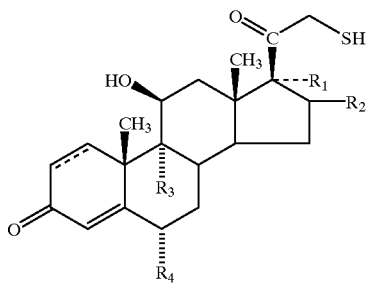
(IV)

and salts thereof, wherein $R_1$, $R_2$, $R_3$, $R_4$ and ⚌ are as defined hereinbefore, with a compound of formula (V) or formula (VI)

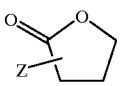
(V)

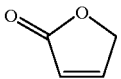
(VI)

wherein Z represents a suitable leaving group (such as Cl, Br or $OSO_2$ A where A is, for example, Me, $CF_3$, p-$MeC_6H_4$), or OH.

Alkylation of a compound of formula (IV) with a compound of formula (V) wherein Z represents a suitable leaving group as defined above may be carried out by application or adaptation of known methods, for example, as described by Mitsukuchi et al. Chem. Pharm. Bull. 1989. 37, 3286–3293.

Thus, alkylation may be performed in the presence of a base such as potassium carbonate or a tertiary amine e.g. triethylamine in a suitable solvent such as tetrahydrofuran, dimethylformamide. dichloromethane, chloroform or a ketone e.g. methyl iso-butyl ketone and under an inert atmosphere such as nitrogen.

Alternatively, alkylation may be performed by reacting a compound of formula (IV) with a compound of formula (V) wherein Z represents OH in the presence of a carbodiimide or the like or using Vilsmeier methodology as described by Barrett and Procopiou, Journal of the Chemical Society, Chemical Communications, 1995, 1403–1404.

The above general process (A) and (B) employing compounds of formula (III) or (V) can be used to prepare compounds of formula (I) in which S is bonded to the alpha, beta or gamma carbon atoms of the lactone group.

Compounds of formula (I) in which S is bonded to the beta carbon atom of the lactone group may also be prepared by reacting a compound of formula (IV) with a compound of formula (VI) by Michael addition in the presence of a base such as potassium carbonate or a tertiary amine e.g. triethylamine and in a suitable solvent such as dimethylformamide or tetrahydrofuran.

Compounds of formula (I) may also be prepared from other compounds of formula (I) using conventional interconversion procedures such as transacetalisation, epimerisation,or esterification. A process for preparing a compound of formula (I) by interconversion of another compound of formula (I) (process C) constitutes yet a further aspect of the present invention.

Compounds of formula (I) having a 1,2 single bond may be prepared by partial reduction of the corresponding 1,2 double bond compound by conventional methods. Thus, for example, by hydrogenation of the corresponding compound of formula (I) or of an intermediate used for the preparation of a compound of formula (I) using a palladium catalyst, conveniently in a suitable solvent e.g. ethyl acetate or preferably by using tris(triphenylphosphine) rhodium (I) chloride (known as Wilkinson's catalyst), conveniently in a suitable solvent such as toluene, ethyl acetate, or ethanol.

It will be appreciated by those skilled in the art that it may be desirable to use protected derivatives of intermediates used in the preparation of compounds of formula (I). Thus, the above processes may require deprotection as an intermediate or final step to yield the desired compound. Thus, according to another process (D), a compound of formula (I) may be prepared by subjecting a protected derivative of a compound of formula (I) to reaction to remove the protecting group or groups present, constituting a further aspect of the present invention.

Protection and deprotection of functional groups may be effected using conventional means. Thus, hydroxyl groups may be protected using any conventional hydroxyl protecting group, for example, as described in Protective Groups in Organic Chemistry, Ed. J. F. W. McOmie (Plenum Press, 1973) or Protective Groups in Organic Synthesis by Theodora W. Green 1991.

Examples of suitable hydroxyl protecting groups include groups selected from alkyl (e.g. t-butyl or methoxymethyl), aralkyl (e.g. benzyl, diphenylmethyl or triphenylmethyl), heterocyclic groups such as tetrahydropyranyl, acyl (e.g. acetyl or benzoyl) and silyl groups such as trialkylsilyl (e.g. t-butyldimethylsilyl). The hydroxyl protecting groups may be removed by conventional techniques. Thus, for example alkyl, silyl, acyl and heterocyclic groups may be removed by solvolysis, e.g. by hydrolysis under acidic or basic conditions. Aralkyl groups such as triphenylmethyl may similarly be removed by solvolysis, e.g. by hydrolysis under acidic conditions. Aralkyl groups such as benzyl may be cleaved by hydrogenolysis in the presence of a Noble metal catalyst such as palladium-on-charcoal.

Compounds of formulae (II), (III), (IV), (V) and (VI) are either generally known compounds or may be prepared by methods analogous to those described in the art for preparing the known compounds of formula (II), (III), (IV), (V) and (VI). Where specific compounds falling within the above general formulae are not known, they may be prepared by the methods described herein or by analogous methods. Novel compounds of formula (II), (III), (IV) and (V) form yet a further aspect of the present invention.

Thus, a compound of formula (II) may be prepared by treating a compound of formula (VII)

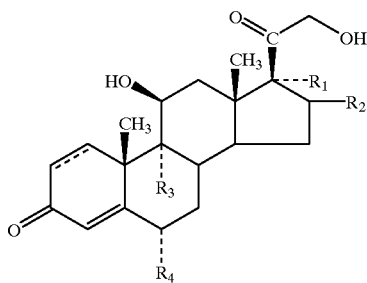

(VII)

(wherein $R_1$, $R_2$, $R_3$, $R_4$ and $\equiv$ are as defined hereinbefore) with a sulfonyl halide such as a sulfonyl chloride e.g methanesulfonyl chloride or tosyl chloride or a sulfonic anhydride e.g. trifluoromethanesulfonic anhydride conveniently under an inert atmosphere such as nitrogen or with the Vilsmeier reagent according to the method of Wuts et al. Synthetic Communications, 1993, 23, 2199–2211.

Compounds of formula (VII) are either commercially available, for example fluocinolone acetonide, budesonide and triamcinolone acetonide are available from Sigma-Aldrich, or can be prepared from the commercially available compounds of formula (VII) by, for example, the transacetalisation methods described in EP0262108 and by partial reduction of the 1,2 double bond compounds by the methods described herein. Alternatively, compounds of formula (VII) can be prepared from commercially available 17α-hydroxyl derivatives of compounds of formula (VII), for example, betamethasone, flumethasone, prednisolone, beclomethasone and dexamethasone available from Sigma-Aldrich, by esterification of the 17α-hydroxyl group according to the method described by Gardi et al, Tetrahedron Letters, 1961, 448.

A compound of formula (IV) may be prepared by treating a compound of formula (VIII)

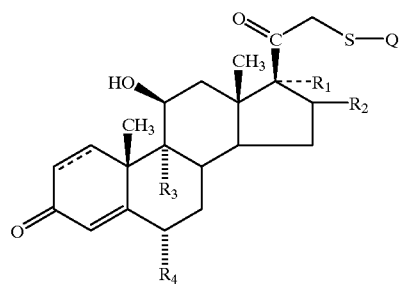

(VIII)

wherein $R_1$, $R_2$, $R_3$, $R_4$ and $\equiv$ are as defined hereinbefore and Q is an acyl group such as acetyl, with a nucleophile such as a hydrazine, ammonia or the like in a suitable solvent such as an ether solvent e.g. tetrahydrofuran.

A compound of formula (VII) may be prepared by treating a compound of formula (VII) defined hereinbefore with a thiolcarboxylic acid such as thiolacetic acid under Mitsunobu conditions using triphenylphosphine and a dialkyl azodicarboxylate.

Alternatively, a compound of formula (VIII) can be prepared by treatment of a compound of formula (II) as defined hereinbefore with thiolacetic acid sodium salt using the methods described by Mitsukuchi et al, Chem. Pharm. Bull, 1989, 37, 3286–3293.

Novel compounds of formulas (VII) and (VIII) form yet a further aspect of the present invention.

Compounds of formula (III), (V) and (VI) are commercially available from Sigma-Aldrich or may be readily prepared by application or adaptation of known methods. For example, α-mercapto-γ-butyrolactone can be prepared by the methods described by G. Fuchs, Ark.Kemi. 1966, 26, 111; β-mercapto-γ-butyrolactone by the methods described by G. Fuchs, Ark.Kemi. 1968, 29, 379; γ-chloro-y-butyrolactone by the methods described by P. Four et al. J. Org. Chem. 1981, 46, 4439; and the chiral α-OH compounds of formula (V) by the methods described by Kenne et al. J. Chem. Soc. Perkin Trans. I, 1988, 1183.

Individual isomers of formula (I) at the point of attachment of the lactone moiety may either be prepared from starting materials having the desired stereochemistry or by epimerisation, resolution or chromatography (e.g. HPLC separation) at an appropriate stage in the synthesis of the required compounds of formula (I) using conventional means.

Thus, for example, it will be appreciated that synthesis employing a racemic mixture of compounds of formula (III) or (V) will afford compounds of formula (I) as a mixture of diastereoisomers, which may then be separated by conventional means, such as chromatography or fractional recrystallisation. Alternatively, the individual diastereoisomers may be prepared by employing compounds of formula (III) or (V) in enantiomerically pure form.

Similarly, compounds of formula (I) in which $R_1$ and $R_2$ together represent

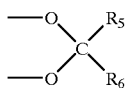

wherein $R_5$ and $R_6$ are different, may exist in the R and S diastereoisomeric forms. Synthesis of such compounds may be stereospecific to yield individual diastereoisomers. Thus, for example, the R-diastereoisomer of a compound of formula (I) wherein $R_5$ represents H and $R_6$ represents n-propyl may be conveniently prepared by transacetalisation of the corresponding 16α,17α-isopropylidenedioxy derivative with butyraldehyde in the presence of an acid catalyst, such as perchloric acid, as described in EP0262108. The transacetalisation reaction may be performed at an intermediate stage or after introduction of the lactone group.

Solvates (e.g. hydrates) of a compound of formula (I) may be formed during work-up procedure of one of the aforementioned process steps. Thus, the compounds of formula (I) may be isolated in association with solvent molecules by crystallisation from or evaporation of an appropriate solvent to give the corresponding solvates. The following Examples illustrate the invention but do not limit the invention in any way.

EXAMPLES

General

The following examples illustrate the preparation of compounds according to the present invention. Melting points were determined on a Kofler block and are uncorrected. $^1$H-nmr spectra were recorded at 250 or 400 MHz and the chemical shifts are expressed in ppm relative to tetramethylsilane. The following abbreviations are used to describe the multiplicities of the signals: s (singlet), d (doublet), t (triplet), q (quartet), m (multiplet), dd (doublet of doublets), dt (doublet of triplets) and b (broad). MS(TSP+ve) and MS(ES+ve) refer to mass spectra run in positive mode using thermospray or electrospray techniques respectively. HRMS (ES+ve) refers to high resolution electrospray mass spectra run in positive mode. TLC (thin layer chromatography) was performed on Merck Kieselgel 60 $F_{254}$ plates and column chromatography was performed on Merck Kieselgel 60 (Art. 7734 or 9385). PLC (preparative layer chromatography) was performed on Whatman silica plates. Preparative HPLC (high performance liquid chromatography) was performed on a Gilson system using the stationary phase indicated in the example. DMF is used as an abbreviation for anhydrous N, N-dimethylformamide.

Where mixtures of isomers resulting from the asymmetric centre in the lactone group have been prepared these isomers may be separated by conventional chromatography on silica and assigned as isomers A and B respectively in order of elution from the column.

Intermediate 1

6α,9α-Difluoro-11β-hydroxy-21-methanesulfonyloxy-16α-methyl-17α-prolionyloxy-pregna-1,4-diene-3,20-dione To a stirring solution of 6α,9α-difluoro-11β,21-dihydroxy-16α-methyl-17α-propionyloxy-pregna-1,4-diene-3,20-dione (2 g, 4.29 mmol) in anhydrous pyridine (20 ml) under a nitrogen atmosphere was added methanesulfonyl chloride (1.66 ml, 21 mmol), dropwise, over 2 minutes. The reaction mixture was stirred for 2 h and was then poured into ice cold 2 M hydrochloric acid (40 ml). The resulting precipitate was collected by filtration, washed with water (30 ml×3) and dried at reduced pressure over phosphorus pentoxide to yield the title compound (2.658 g, quantitative yield): mp 185–187° C.; MS (TSP+ve) m/z 545 $(M+H)^+$; IR $\nu_{max}$ (KBr) 3544, 1731. 1667, 1633 cm$^{-1}$; NMR δ (DMSO-d$_6$) includes 7.25 (1H, d, J 10 Hz), 6.30 (1H. d, J 10 Hz), 6.11 (1H, s), 5.73 and 5.53 (1H, 2 m), 5.54 (1H, bs), 5.07 (1H. d. J 16 Hz), 4.83 (1H,d J 16 Hz), 4.18 (1H, m), 3.26 (3H, s), 3.23 (1H, m), 2.40 (2H, q, J 7.5 Hz), 1.48 (3H, s), 1.00 (3H, t, J 7.5 Hz), 0.96 (3H, s), 0.85 (3H. d, J 7 Hz). (Found: C, 56.99; H, 6.27; S, 5.43. $C_{26}H_{34}F_2O_8S.0.3H_2O$ requires C, 56.78; H, 6.34; S, 5.83%).

Intermediate 2

21-Acetylsulfanyl-6α,9α-difluoro-11β-hydroxy-16α-methyl-17α-propionyloxy-pregna-1,4-diene-3, 20-dione To a stirring solution of triphenylphosphine (380 mg, 1.45 mmol) in anhydrous tetrahydrofuran (3.5 ml) at 0° C. under a nitrogen atmosphere was added diisopropyl azodicarboxylate (285 µl, 1.45 mmol). The resulting white suspension was stirred at 0–5° C. for 1 h after which time a solution of 6α,9α-difluoro-11β,21-dihydroxy-16α-methyl-17α-propionyloxy-pregna-1,4-diene-3,20-dione (450 mg, 0.97 mmol) and thiolacetic acid (103 µl, 1.45 mmol) in anhydrous tetrahydrofuran (3.5 ml) was added, dropwise, over 10 minutes. The reaction mixture was stirred for a further 1 h at 0–5° C. and for 4 h at 21° C. The solvent was removed under reduced pressure and the residue was separated between ethyl acetate (50 ml) and 0.5 M hydrochloric acid (50 ml). The organic layer was washed with water (50 ml), saturated sodium bicarbonate solution (50 ml), water (50 ml) and saturated brine (50 ml). The solution was then dried over anhydrous magnesium sulfate and the solvent was removed under reduced pressure. The residue was purified by column chromatography eluting with ethyl acetate-40–60 petroleum ether (2:3). Removal of the solvent from appropriate fractions under reduced pressure gave the title compound (292 mg, 57%): mp 205–210° C.; MS (ES+ve) m/z 525 $(M+H)^+$; IR $\nu_{max}$ (KBr) 1727, 1694, 1667, 1629 cm$^{-1}$; NMR δ (CDCl$_3$) includes 7.11 (1H, d, J 10 Hz), 6.44 (1H, s), 6.38 (1H, d, J 10 Hz), 5.49 and 5.29 (1H, 2m), 4.40 (1H, m), 4.24 (1H, d, J 17 Hz), 3.54–3.30 (1H. m), 3.47 (1H, d, J 17 Hz), 2.40 (3H, s), 2.39 (2H, q, J 7.5 Hz), 1.53 (3H, s), 1.14 (3H, t, J 7.5 Hz), 1.05 (3H, s), 0.95 (3H, d, J 7.5 Hz). (Found: C, 62.06; H, 6.52. $C_{27}H_{34}F_2O_6S$ requires C, 61.82; H, 6.53%).

Intermediate 3

6α, 9α-Difluoro-11β-hydroxy-21-mercapto-16α-methyl-17α-propionyloxy-pregna-1,4-diene-3,20-dione To a stirring solution of 21-acetylsulfanyl-6α,9α-difluoro-11β-hydroxy-16α-methyl-17α-propionyloxy-pregna-1,4-diene-3,20-dione (Intermediate 2, 250 mg, 0.48 mmol) in anhydrous tetrahydrofuran (3 ml) at −15° C. was added hydrazine hydrate (30 µl, 0.52 mmol). The resulting reaction mixture was stirred at −15 to −10° C. for 1 h. The solvent was removed under reduced pressure yielding a residue which was separated between ethyl acetate (50 ml) and 0.5 M hydrochloric acid (50 ml). The organic layer was then washed with water (50 ml), saturated sodium bicarbonate solution (50 ml), water (50 ml) and saturated brine (50 ml). The solution was then dried over anhydrous magnesium sulfate and the solvent was removed under reduced pressure to yield a pale yellow solid. This material was purified by preparative reverse phase HPLC (Dynamax 60 ÅC18, 25 cm×41 mm i.d.) eluting with 50–95% acetonitrile/water with detection at 230 nm. Removal of the solvent from appropriate fractions under reduced pressure yielded the title compound as a pale yellow solid (96 mg, 42%): mp 223–227° C.; MS (ES+ve) m/z 483 (M+H)$^+$; NMR δ (CDCl$_3$) includes 7.10 (1H, d, J 10 Hz), 6.44 (1H, s), 6.38 (1H, d, J 10 Hz), 5.48 and 5.28 (1H, 2m), 4.41 (1H, m), 3.46–3.20 (3H, m), 2.40 (2H, q, J 7.5 Hz), 1.52 (3H, s), 1.18 (3H, t, J 7.5 Hz), 1.07 (3H, s), 0.93 (3H, d, J 7.5 Hz). (Found: C, 62.23; H, 6.78; S, 6.36. $C_{25}H_{32}F_2O_5S$ requires C, 62.22; H, 6.68; S, 6.64%).

Intermediate 4

6α,9αDifluoro-11β,21-dihydroxy-16α-methyl-17α-propionyloxy-pregn-4-ene-3,20-dione A stirring solution of 6α,9α-difluoro-11β,21-dihydroxy-16α-methyl17α-propionyloxy-pregna-1,4-diene-3,20-dione (3 g, 6.43 mmol) and tris-(triphenylphosphine) rhodium (I) chloride (0.6 g, 0.64 mmol) in ethanol (100 ml) was hydrogenated at 1 atmosphere for 60 h. The solvent was then removed under reduced pressure to give a residue which was purified by column chromatography eluting with ethyl acetate-cyclohexane (3:1). Removal of the solvent from appropriate fractions under reduced pressure yielded the title compound as a pale yellow solid (2.57 g, 85%): mp 175–190° C.; MS (TSP+ve) m/z 469 (M+H)$^+$; IR $\nu_{max}$ (KBr) 3428, 1730, 1717, 1669 cm$^{-1}$; NMR δ (DMSO-d$_6$) includes 5.82 (1H, s), 5.60 and 5.42 (1H, 2m), 5.20 (1H bs), 5.07 (1H, t, J 6 Hz), 4.25–3.95 (3H, m), 3.24 (1H, m), 2.39 (2H, q, J 7.5 Hz), 1.48 (3H, s), 1.03 (3H, t, J 7.5 Hz), 0.90 (3H, s), 0.84 (3H, d, J 7 Hz); HRMS (ES+ve) found 469.240056, (M+H)$^+$. $C_{25}H_{35}F_2O_6$ requires 469.24171.

Intermediate 5

6α,9α-Difluoro-11β-hydroxy-21-methanesulfonyloxy-16α-methyl-17α-propionyloxy-pregn-4-ene-3,20-dione To a stirring solution of 6α,9α-difluoro-11β,21-dihydroxy-16α-methyl-17α-propionyloxy-pregn-4-ene-3,20-dione (Intermediate 4, 2 g, 4.27 mmol) in anhydrous pyridine (20 ml) under a nitrogen atmosphere was added methanesulfonyl chloride (1.66 ml, 21 mmol), dropwise, over 2 minutes. The reaction mixture was stirred for 2 h and was then poured into ice cold 2 M hydrochloric acid (40 ml). The resulting precipitate was collected by filtration, washed with water (30 ml×3) and dried at reduced pressure over phosphorus pentoxide to yield the title compound (2.390 g, quantitative yield): Mp 157–159° C. (decomp); MS (TSP+ve) m/z 547 (M+H)$^+$; IR $\nu_{max}$ (KBr) 3532, 1731, 1668 cm$^{-1}$; NMR δ (DMSO-d$_6$) includes 5.81 (1H, s), 5.60 and 5.41 (1H, 2 m), 5.24 (1H, bs), 5.05 (1H, d, J 16 Hz), 4.82 (1H, d, J 16 Hz), 4.16 (1H, m), 3.26 (3H, s), 2.43 (2H, q, J 7.5 Hz), 1.48 (3H, s), 1.02 (3H, t, J 7.5 Hz), 0.94 (3H, s), 0.85 (3H, d, J 7 Hz). (Found: C, 56.12; H, 6.54; S, 5.67. $C_{26}H_{36}F_2O_8S.0.5H_2O$ requires C, 56.39; H, 6.70; S, 5.79%).

Intermediate 6

Methanesulfonic acid 2-oxo-tetrahydro-furan-3R-yl ester

To a stirring solution of (R)-3-hydroxy-2-oxo-tetrahydrofuran (400 mg, 3.92 mmol) and triethylamine (601 µl, 4.31 mmol) in anhydrous dichloromethane (15 ml) at 0° C. under a nitrogen atmosphere was added methanesulfonyl chloride (334 µl, 4.31 mmol). The resulting mixture was stirred at 0° C. for 0.25 h and at 21° C. for 2.5 h. Further quantities of triethylamine (109 µl, 0.78 mmol) and methanesulfonyl chloride (61 µl, 0.78 mmol) were added and the mixture stirred for 1.5 h. The reaction mixture was poured into water (20 ml) and the separated aqueous layer was extracted with dichloromethane (20 ml). The combined organic layers were washed with saturated sodium bicarbonate solution (20 ml) and saturated brine (20 ml) then dried over anhydrous magnesium sulfate. The solvent was removed under reduced pressure yielding a yellow residue which was purified by flash column chromatography on silica gel using ethyl acetate:cyclohexane (3:2) as eluent. Removal of the solvent from appropriate fractions under reduced pressure gave the title compound as a white crystalline solid (214 mg, 30%): mp 69–72 ° C.; MS (TSP+ve) m/z 198 (M+NH$_4$)$^+$; IR $\nu_{max}$ (KBr) 1774, 1363 cm$^{-1}$; NMR δ (CDCl$_3$) 5.33 (1H, t, J 9 Hz), 4.53 (1H, dt, J 9 and 3.5 Hz), 4.43–4.28 (1H, m), 3.30 (3H, s), 2.88–2.72 (1H, m), 2.66–2.47 (1H, m). (Found: C, 33.53; H, 4.16; S, 17.35. $C_5H_8O_5S.0.05H_2O$ requires C, 33.17; H, 4.51; S, 17.71%).

Intermediate 7

Methanesulfonic acid 2-oxo-tetrahydro-furan-3S-yl ester

To a stirring solution of (S)-3-hydroxy-2-oxo-tetrahydrofuran (500 mg, 4.90 mmol) and triethylamine (0.88 ml, 6.37 mmol) in anhydrous dichloromethane (20 ml) at 0° C. under a nitrogen atmosphere was added methanesulfonyl chloride (0.49 ml, 6.37 mmol). The resulting mixture was stirred at 0° C. for 0.5 h and at 21° C. for a further 5 h. The solvent was removed from the reaction mixture under reduced pressure yielding a residue which was purified by flash column chromatography on silica gel using ethyl acetate-:cyclohexane (3:2) as eluent. Removal of the solvent from appropriate fractions under reduced pressure gave the title compound as a white crystalline solid (341 mg, 39%): mp 74–76° C.; MS (TSP+ve) m/z 198 (M+NH$_4$)$^+$; IR $\nu_{max}$ (KBr) 1787, 1363 cm$^{-1}$; NMR δ (CDCl$_3$) 5.34 (1H, t, J 9 Hz), 4.53 (1H, dt, J 9 and 3 Hz), 4.41–4.28 (1H, m), 3.29 (3H, s), 2.86–2.71 (1H, m), 2.66–2.47 (1H, m). (Found: C, 33.47; H, 4.86; S, 17.80. $C_5H_8O_5S$ requires C, 33.33; H, 4.48; S, 17.80%).

Intermediate 8

6α,9α-Difluoro-11β-hydroxy-16α,17α-isopropylidenedioxy-21-methanesulfonyloxy-pregn-4-ene-3,20-dione To a stirring solution of 6α,9α-difluoro-11β,21-dihydroxy-16α,17α-isopropylidenedioxy-pregn-4-ene-3,20-dione (1 g, 2.2 mmol) in anhydrous pyridine (10 ml) at 0° C. under a nitrogen atmosphere was added methanesulfonyl chloride (0.85 ml, 11 mmol). The reaction mixture was stirred for 2 h and was then poured into ice cold 1M hydrochloric acid (40 ml). The resulting suspension was extracted with ethyl acetate (20 ml×4) and the combined organic extracts were washed with saturated brine (20 ml) and dried over anhydrous magnesium sulfate. Removal of the solvent under reduced pressure yielded a pale yellow residue which was purified by preparative reverse phase HPLC (Dynamax 60 ÅC18, 25 cm×41 mm i.d.) eluting with 55% acetonitrile/water at 45 ml/min with detection at 230 nm. Appropriate fractions were combined and the solvent was removed under reduced pressure to yield a colourless foam, the title compound (843 mg, 72%): MS (ES+ve) m/z 533 (M+H)$^+$; IR $v_{max}$ (KBr) 3453, 1732, 1669 cm$^{-1}$; NMR δ (DMSO-d$_6$) includes 5.80 (1H, s), 5.61 and 5.42 (1H, 2m), 5.35 (1H, J 18 Hz), 5.30 (1H, bs), 4.93 (1H, bs), 4.90 (1H, d, J 18 Hz), 4.19 (1H, m), 3.32 (3H, s), 1.48 (3H, s), 1.38 (3H, s), 1.15 (3H, s), 0.80 (3H, s). (Found: C, 55.66; H, 6.29; S, 5.87. $C_{25}H_{34}F_2O_8S.0.4H_2O$ requires C, 55.63; H, 6.50; S, 5.94%).

Intermediate 9

16α,17α-(R-Butylidenedioxy)-6α,9α-difluoro-11β-hydroxy-21-methanesulfonyloxy-pregna-1,4-diene-3,20-dione To a stirring solution of 16α,17α-(R-butylidenedioxy)-6α,9α-difluoro-11β,21-dihydroxy-pregna-1,4-diene-3,20-dione (500 mg, 1.07 mmol) in anhydrous pyridine (6 ml) under a nitrogen atmosphere was added methanesulfonyl chloride (0.41 ml, 5.35 mmol). The reaction mixture was stirred for 2 h and was then poured into ice cold 1 M hydrochloric acid (30 ml). The resulting precipitate was collected by filtration and dried at reduced pressure over phosphorus pentoxide to yield a pale yellow solid, the title compound (566 mg, 97%): MS (TSP+ve) m/z 545 (M+H)$^+$; NMR δ (DMSO-d$_6$) includes 7.27 (1H, d, J 10 Hz), 6.30 (1H, d, J 10 Hz), 6.10 (1H, s), 5.73 and 5.53 (1H, 2 m), 5.61 (1H, bs), 5.27 (1H, d, J 18 Hz), 4.99 (1H, d, J 18 Hz), 4.75 (2H, m), 4.20 (1H, bs), 3.29 (3H, s), 1.48 (3H, s), 0.87 (3H, t, J 7.5 Hz), 0.84 (3H, s). (Found: C, 56.39; H, 6.22; S, 6.03. $C_{26}H_{34}F_2O_8S.0.4H_2O$ requires C, 56.59; H. 6.36; S. 5.81%).

Intermediate 10

16α,17α-(R-Butylidenedioxy)-6α,9α-difluoro-11β-hydroxy-21-methanesulfonyloxy-pregn-4-ene-3,20-dione To a stirring solution of 16α,17α-(R-butylidenedioxy)-6α,9α-difluoro-11β,21-dihydroxy-pregn-4ene-3,20-dione (1 g, 2.13 mmol) in anhydrous pyridine (12 ml) at 0° C. under a nitrogen atmosphere was added methanesulfonyl chloride (0.82 ml, 10.65 mmol). The reaction mixture was stirred for 0.5 h at 0° C. and 2.5 h at 21° C. and was then poured into ice cold 1M hydrochloric acid (60 ml). The resulting precipitate was collected by filtration and dried at reduced pressure over phosphorus pentoxide to yield a pale yellow solid which was purified by preparative reverse phase HPLC (Dynamax 60 ÅC18, 25 cm×41 mm i.d.) eluting with 55% acetonitrile/water at 45 ml/min with detection at 230 nm. Appropriate fractions were combined and evaporated under reduced pressure to yield the title compound (730 mg, 63%): MS (TSP+ve) m/z 547 (M+H)$^+$; NMR δ (CDCl$_3$) includes 6.15 (1H, s), 5.37 and 5.18 (1H, 2m), 5.04 (2H, s), 4.89 (1H, d, J 5 Hz), 4.65 (1H, t, J 4.5 Hz), 4.41 (1H, m), 3.26 (3H ,s), 1.52 (3H, s), 0.95 (3H, t, J 7.5 Hz), 0.94 (3H, s). (Found: C, 56.58; H, 6.40; S, 5.76. $C_{26}H_{36}F_2O_8S.0.3H_2O$ requires C, 56.57; H, 6.68; S, 5.81%).

Intermediate 11

6α,9α-Difluoro-11β-hydroxy-16α,17α-isopropylidenedioxy-21-trifluoro-methanesulfonyloxy-pregna-1,4-diene-3,20-dione To a stirring solution of 6α,9α-difluoro-11β,21-dihydroxy-16α,17α-isopropylidenedioxy-pregna-1,4-diene-3,20-dione (5 g, 11.1 mmol) and pyridine (1.8 ml, 22.2 mmol) in dichloromethane (50 ml) at −20° C. under a nitrogen atmosphere was added trifluoromethanesulfonic anhydride (2.23 ml, 13.3 mmol). The reaction mixture was stirred for 0.5 h during which time it warmed up to 20° C. and was then poured into 2M hydrochloric acid (100 ml) and extracted with ethyl acetate (200 ml). The organic phase was washed with water (100 ml), saturated brine (100 ml) and dried over anhydrous magnesium sulfate. Removal of the solvent under reduced pressure and trituration in diethyl ether (30 ml) yielded the title compound (6.2 g, 96%): NMR δ (DMSO-d$_6$) includes 7.29 (1H, d, J 10 Hz), 6.31 (1H, d, J 10 Hz), 6.11 (1H, s), 5.80 (1H, d, J 18 Hz), 5.74 and 5.54 (1H, 2m), 5.61 (1H, d, J 5 Hz), 5.45 (1H, d, J 18 Hz), 4.93 (1H, d, J 3 Hz), 4.21 (1H, m), 1.48 (3H, s), 1.37 (3H, s), 1.15 (3H, s), 0.83 (3H, s).

Intermediate 12

21-Acetylsulfanyl-16α,17α-(R-butylidenedioxy)-6α,9α-difluoro-11β-hydroxy-pregn-4-ene-3,20-dione To a stirring solution of triphenylphosphine (1.21 g, 4.62 mmol) in anhydrous tetrahydrofuran (20 ml) at 0° C. under a nitrogen atmosphere was added diisopropyl azodicarboxylate (0.91 ml, 4.62 mmol). The resulting yellow suspension was stirred at 0–5° C. for 0.5 h after which time a solution of 16α,17α-(R-butylidenedioxy)-6α,9α-difluoro-11β,21-dihydroxy-pregn4-ene-3,20-dione (1.40 g, 3.08 mmol) and thiolacetic acid (0.26 ml, 3.70 mmol) in anhydrous tetrahydrofuran (10 ml) was added dropwise over 15 min. The reaction mixture was stirred for a further 0.5 h at 0–5° C. and for 18 h at 20° C. The reaction mixture was poured into 2 M hydrochloric acid (100 ml) and extracted with ethyl acetate (100 ml). The organic phase was washed with aqueous sodium bicarbonate solution (100 ml), water (100 ml), and saturated brine (100 ml) and dried over anhydrous magnesium sulfate. Removal of the solvent under reduced pressure yielded a yellow solid. The crude product was purified by column chromatography on silica gel using ethyl acetate-cyclohexane (2:3) as eluent. Removal of the solvent from the required fractions gave the title compound (1.63 g, 100%): MS (TSP+ve) m/z 527 (M+H)$^+$; NMR δ (CDCl$_3$) includes 6.16 (1H, s), 5.37 and 5.18 (1H, 2 m), 4.90 (1H, d, J 5 Hz), 4.68 (1H, t, J 4 Hz), 4.42 (1H, m), 3.94 (2H, s), 2.40 (3H, s), 1.52 (3H, s), 0.95 (3H, t, J 6 Hz), 0.90 (3H, s).

Intermediate 13

16α,17α-(R-Butylidenedioxy)-6α,9α-difluoro-11β-hydroxy-21-mercapto-pregn-4-ene-3,20-dione To a stirring solution of 21-acetylsulfanyl-16α,17α-(R-butylidenedioxy)-6α,9α-difluoro-11β-hydroxy-pregn-4-ene-3,20-dione (Intermediate 12, 1.62 g, 3.08 mmol) in anhydrous tetrahydrofuran (25 ml) at −15°0 C. under a nitrogen atmosphere was added hydrazine hydrate (0.18 ml, 3.08 mmol). The reaction mixture was stirred at −15 to −10° C. for 0.5 h and then at 20 °C. for 5 h. The reaction mixture was poured into 2 M hydrochloric acid (75 ml) and extracted with ethyl acetate (75 ml). The organic phase was washed with water (75 ml), and saturated brine (75 ml) and dried over anhydrous magnesium sulfate. Removal of the solvent under reduced pressure yielded the title compound (1.35 g, 91%): MS (TSP+ve) m/z 485 (M+H)$^+$; NMR δ (CDCl$_3$) includes 6.15 (1H, s), 5.37 and 5.18 (1H, 2m), 4.94 (1H, d, J 5 Hz), 4.65 (1H, t, J 4 Hz), 4.40 (1H, m), 3.68 (1H, dd, J 16 and 7 Hz), 3.42 (1H, dd, J 16 and 7 Hz), 1.52 (3H, s), 0.94 (3H, t, J 6 Hz), 0.89 (3H, s).

EXAMPLE 1

6α,9α-Difluoro-11β-hydroxy-16α-methyl-21-(2-oxo-tetrahydro-furan-3-yl-sulfanyl)-17α-propionyloxy-pregna-1,4-diene-3,20-dione Method 1

To a stirring suspension of sodium hydride (74 mg of 60% w/w dispersion in mineral oil, 1.84 mmol) in anhydrous tetrahydrofuran (2 ml) at 0° C. under a nitrogen atmosphere was added dropwise a solution of α-mercapto-γ-butyrolactone (220 mg, 1.84 mmol) in anhydrous tetrahydrofuran (10 ml). The resulting solution was stirred at 0° C. for 30 minutes by which time effervescence had ceased. A solution of 6α,9α-difluoro-11β-hydroxy-21-methanesulfonyloxy-16α-methyl-17α-propionyloxy-pregna-1,4-diene-3,20-dione (Intermediate 1, 1 g, 1.84 mmol) in anhydrous tetrahydrofuran (20 ml) was added and the reaction mixture was stirred for 16 h at 0–21° C. Further quantities of sodium hydride (37 mg of 60% w/w dispersion in mineral oil, 0.92 mmol) and α-mercapto-γ-butyrolactone (110 mg, 0.92 mmol) were added and the mixture stirred for another 6 h. The reaction mixture was poured into water (30 ml) and extracted with ethyl acetate (30 ml×4). The combined organic extracts were then washed with saturated brine (20 ml) and dried over anhydrous magnesium sulfate. Removal of the solvent under reduced pressure yielded a pale yellow residue which was purified by preparative reverse phase HPLC (Dynamax 60 ÅC18, 25 cm×41 mm i.d.) eluting with 50% acetonitrile/water at 45 ml/min with detection at 230 nm. Appropriate fractions were combined and evaporated under reduced pressure to yield the title compound (177 mg, 17%): mp 197–206° C.; MS (ES+ve) m/z 567 (M+H)$^+$; IR $v_{max}$ (KBr) 3484, 2949, 1761, 1731, 1669, 1629 cm$^{-1}$; NMR δ (CDCl$_3$) includes 7.14 (1H, d, J 10 Hz), 6.44 (1H, s), 6.38 (1H, d, J 10 Hz), 5.49 and 5.30 (1H, 2m), 4.53–4.28 (3H, m), 4.00–3.75 (3H, m), 3.60–3.30 (2H, m), 2.43 (1H, q, J 7.5 Hz), 2.40 (1H, q, J 7.5 Hz), 1.53 (3H, s), 1.14 (3H, t, J 7.5 Hz), 1.06 (3H, s), 0.94 (3H, d, J 7.5 Hz). (Found: C, 61.60; H, 6.30; S, 5.75. $C_{29}H_{36}F_2O_7S$ requires C, 61.47; H, 6.40; S, 5.66%).

Method 2

To a stirring suspension of 6α,9α-difluoro-11β-hydroxy-21-mercapto-16α-methyl-17α-propionyloxy-pregna-1,4-diene-3,20-dione (Intermediate 3, 85 mg, 0.18 mmol) in dichloromethane (3 ml) under a nitrogen atmosphere was added triethylamine (74 μl, 0.53 mmol). The suspension was then cooled to 0° C. and α-bromo-γ-butyrolactone (45 μl, 0.53 mmol) was added. The resulting reaction mixture was then stirred at 0–21° C. for 4 h. The solvent was removed from the mixture under reduced pressure and the residue was separated between ethyl acetate (50 ml) and 0.5 M hydrochloric acid (50 ml). The organic layer was washed with water (50 ml×2) and saturated brine (50 ml) and was then dried over anhydrous magnesium sulfate. Removal of the solvent under reduced pressure yielded a pale yellow residue which was purified by reverse phase HPLC (Dynamax 60 ÅC18, 25 cm×41 mm i.d) eluting with 50–95% acetonitrile/water at 45 ml/min with detection at 230 nm. Appropriate fractions were combined and evaporated under reduced pressure to yield the title compound (30 mg, 30%): mp 198–205° C.; MS (TSP+ve) m/z 567 (M+H)$^+$; IR $v_{max}$ (KBr) 1759, 1730, 1712, 1631 cm$^{-1}$; NMR δ (CDCl$_3$) includes 7.11 (1H, d, J 10 Hz), 6.44 (1H, s), 6.38 (1H, d, J 10 Hz), 5.48 and 5.28 (1H, 2 m), 4.52–4.28 (3H, m), 4.00–3.74 (2H, m), 3.63–3.30 (2H, m), 1.52 (3H, s), 1.15 (3H, t. J 7.5 Hz), 1.05 (3H, s), 0.94 (3H, d, J 7 Hz). (Found: C, 61.67; H, 6.79; S, 5.27. $C_{29}H_{36}F_2O_7S$ requires C, 61.47; H, 6.40; S, 5.66%).

EXAMPLE 2

6α,9α-Difluoro-11β-hydroxy-16α-methyl-21-(2-oxo-tetrahydro-furan-3-yl-sulfanyl)-17α-propionyloxy-pregn-4-ene-3,20-dione To a stirring suspension of sodium hydride (74 mg of 60% w/w dispersion in mineral oil, 1.84 mmol) in anhydrous tetrahydrofuran (2 ml) at 0° C. under a nitrogen atmosphere was added, dropwise, a solution of α-mercapto-γ-butyrolactone (220 mg, 1.84 mmol) in anhydrous tetrahydrofuran (10 ml). The resulting solution was stirred at 0° C. for 30 minutes by which time effervescence had ceased. A solution of 6α,9α-difluoro-11β-hydroxy-21-methanesulfonyloxy-16α-methyl-17α-propionyloxy-pregn-4-ene-3,20-dione (Intermediate 5, 1 g. 1.84 mmol) in anhydrous tetrahydrofuran (20 ml) was added and the reaction mixture was stirred for 16 h at 0–21° C. Further quantities of sodium hydride (37 mg of 60% w/w dispersion in mineral oil. 0.92 mmol) and α-mercapto-γ-butyrolactone (110 mg, 0.92 mmol) were added and the mixture stirred for another 6 h. The reaction mixture was poured into water (30 ml) and extracted with ethyl acetate (30 ml×4). The combined organic extracts were then washed with saturated brine (20 ml) and dried over anhydrous magnesium sulfate. Removal of the solvent under reduced pressure yielded a yellow residue which was purified by preparative reverse phase HPLC (Dynamax 60 ÅC18, 25 cm×41 mm i.d.) eluting with 55% acetonitrile/water at 45 ml/min with detection at 230 nm. Appropriate fractions were combined and evaporated under reduced pressure to yield the title compound (455 mg, 43%): mp 171–175° C.; MS (ES+ve) m/z 569 (M+H)$^+$; IR $v_{max}$ (KBr) 3505, 1757, 1732, 1669 cm$^{-1}$; NMR δ (CDCl$_3$) includes 6.14 (1H, s), 5.37 and 5.18 (1H, 2m), 4.52–4.26 (3H, m), 4.03–3.74 (2H, m), 3.59–3.32 (2H, m), 1.52 (3H, s), 1.17 (3H, t, J 7.5 Hz), 1.03 and 1.02 (3H, 2s), 0.94 (3H, d, J 7 Hz). (Found: C, 61.24; H, 7.08; S, 5.54. $C_{29}H_{38}F_2O_7S$ requires C, 61.25; H, 6.74; S, 5.64%).

EXAMPLE 3

6α,9α-Difluoro-11β-hydroxy-16α,17α-isopropylidenedioxy-21-(2-oxo-tetrahydro-furan-3-yl-sulfanyl)-pregna-1,4-diene-3,20-dione Method 1

To a stirring suspension of sodium hydride (27 mg of 60% w/w dispersion in mineral oil, 0.68 mmol) in anhydrous tetrahydrofuran (1 ml) at 0° C. under a nitrogen atmosphere was added, dropwise, a solution of α-mercapto-γ-butyrolactone (80 mg, 0.68 mmol) in anhydrous tetrahydrofuran (2 ml). The resulting solution was stirred at 0° C. for 30 minutes by which time effervescence had ceased. A solution of 6α,9α-difluoro-11β-hydroxy-16α,17α-isopropylidenedioxy-21-methanesulfonyloxy-pregna-1,4-diene-3,20-dione (300 mg, 0.57 mmol) in anhydrous tetrahydrofuran (10 ml) was added and the reaction mixture was stirred for a further 1 h at 0–21° C. The reaction mixture was poured into water (30 ml) and extracted with ethyl acetate (10 ml ×3). The combined organic extracts were washed with saturated brine (20 ml) and dried over anhydrous magnesium sulfate. Removal of the solvent under reduced pressure yielded a white solid which was purified by preparative reverse phase HPLC (Dynamax 60 ÅC18, 25 cm×41 mm i.d.) eluting with 50% acetonitrile/water at 45 ml/min with detection at 230 nm. Appropriate fractions were combined and evaporated under reduced pressure to yield title compound. isomer A (87.6 mg, 28%): mp 226–229° C.; MS (TSP+ve) m/z 553 (M+H)$^+$; IR $v_{max}$ (KBr) 1766, 1716, 1668 cm$^{-1}$; NMR δ (DMSO-d$_6$) includes 7.30 (1H, d, J 10 Hz), 6.30 (1H, d, J 10 Hz), 6.11 (1H, s), 5.74 and 5.54 (1H, 2 m), 5.60 (1H, d, J 4.5 Hz), 4.91 (1H, bs), 4.39–4.15 (3H, m), 4.22 (1H, d, J 17.5 Hz), 3.93 (1H, dd, J 8 and 6 Hz), 3.83 (1H, d, J 17.5 Hz), 1.48 (3H, s), 1.35 (3H, s), 1.08 (3H, s), 0.82 (3H, s). (Found: C, 60.02; H, 6.14; S, 5.64. $C_{28}H_{34}F_2O_7S.0.5H_2O$ requires C, 59.88; H, 6.28; S 5.71%) title compound. isomer B (72 mg, 23%): mp 204–205° C.;

MS (TSP+ve) m/z 553 (M+H)$^+$; IR $\nu_{max}$ (KBr) 3474, 1759, 1719, 1668, 1633 cm$^{-1}$; NMR δ (DMSO-d$_6$) includes 7.30 (1H, d, J 10 Hz), 6.30 (1H, d, J 10 Hz), 6.11 (1H, S), 5.74 and 5.54 (1H, 2 m), 5.58 (1H. bs), 4.91 (1H, bs), 4.39–4.15 (4H, m), 3.91 (1H, dd, J 8 and 6.5 Hz), 3.82 (1H, d, J 17.5 Hz), 1.48 (3H, s), 1.36 (3H, s), 1.12 (3H, s), 0.79 (3H, s). (Found: C, 58.82; H, 6.99; S, 5.67. C$_{28}$H$_{34}$F$_2$O$_7$S.H$_2$O.C$_2$H$_3$N requires C, 58.91; H, 6.43; S, 5.24%).

Method 2

To a stirring suspension of 6α,9α-difluoro-11β-hydroxy-21-mercapto-16α,17α-isopropylidenedioxy-pregna 1,4-diene-3,20-dione (50 mg, 0.11 mmol) in dichloromethane (1 ml) under a nitrogen atmosphere was added triethylamine (45 μl, 0.32 mmol). The suspension was then cooled to 0° C. and α-bromo-γ-butyrolactone (27 μl, 0.32 mmol) was added. The resulting reaction mixture was then stirred at 0–21° C. for 4 h. The solvent was removed from the mixture under reduced pressure and the residue was separated between ethyl acetate (25 ml) and 0.5 M hydrochloric acid (25 ml). The organic layer was washed with water (25 ml×2) and saturated brine (25 ml) and was then dried over anhydrous magnesium sulfate. Removal of the solvent under reduced pressure yielded a colourless residue which was purified by reverse phase HPLC (Dynamax 60 ÅC18, 25 cm×41 mm i.d) eluting with 50–95% acetonitrile/water at 45 ml/min with detection at 230 nm. Appropriate fractions were combined and evaporated under reduced pressure to yield title compound, isomer A (27 mg, 46%): mp 224–228° C.; MS (TSP+ve) m/z 553 (M+H)$^+$; IR $\nu_{max}$ (KBr) 3391, 1763, 1716, 1667, 1609 cm$^{-1}$; NMR δ (CDCl$_3$) includes 7.12 (1H, d, J 10 Hz) 6.44 (1H, s), 6.37 (1H, d, J 10 Hz), 5.48 and 5.29 (1H, 2 m), 5.06 (1H, d, J 4.5 Hz), 4.55–4.33 (3H, m), 4.04 (1H, d, J 19 Hz), 3.88 (1H, d, J 19 Hz), 3.83 (1H, dd, J 8.5 and 3.5 Hz), 1.53 (3H, s), 1.43 (3H, s), 1.16 (3H, s), 0.94 (3H, s) and title compound, isomer B (29 mg, 49%): mp 203–206° C.; MS (TSP+ve) m/z 533 (M+H)$^+$; IR $\nu_{max}$ (KBr) 3437, 1762, 1715, 1669, 1628 cm$^{-1}$; NMR δ (CDCl$_3$) includes 7.12 (1H, d, J 10 Hz), 6.44 (1H, s), 6.38 (1H, d, J 10 Hz), 5.48 and 5.29 (1H, 2m), 5.05 (1H, d, J 4.5 Hz) 4.55–4.30 (3H, m), 4.27 (1H, d, J 17.5 Hz), 3.93 (1H, d, J 17.5 Hz), 3.68 (1H, dd, J 8 and 4.5 Hz), 1.53 (3H, s), 1.43 (3H, s) 1.19 (3H, s), 0.90 (3H, s).

EXAMPLE 4

6α,9α-Difluoro-11β-hydroxy-16α,17α-isopropylidenedioxy-21-(2-oxo-tetrahydro-furan-3S-yl-sulfanyl)-pregna-1,4-diene-3,20-dione To a stirring suspension of sodium hydride (9 mg of a 60% w/w dispersion in mineral oil, 0.21 mmol) in anhydrous DMF (1 ml) at 0° C. under a nitrogen atmosphere was added a solution of 6α,9α-difluoro-11β-hydroxy-21-mercapto-16α,17α-isopropylidenedioxy-pregna-1,4-diene-3,20-dione (100 mg, 0.21 mmol) in anhydrous DMF (2 ml). The resulting mixture was stirred at 0° C. for 0.5 h at which point a solution of methanesulfonic acid 2-oxo-tetrahydro-furan-3R-yl ester (Intermediate 6, 38 mg, 0.21 mmol) in anhydrous DMF (3 ml) was added. The reaction mixture was stirred at 0° C. for 0.5 h and at 21° C. for a further 1 h. The mixture was partitioned between water (20 ml) and ethyl acetate (20 ml). The aqueous layer was extracted with ethyl acetate (20 ml) and the combined organic extracts were washed with saturated brine (20 ml), dried over anhydrous magnesium sulfate and evaporated under reduced pressure to yield a yellow oily residue. This material was purified by flash column chromatography on silica gel using ethyl acetate as eluent. Removal of the solvent from appropriate fractions under reduced pressure gave the title compound as a white solid (38 mg, 32%); spectroscopic data were identical to those obtained for isomer A in Example 3.

EXAMPLE 5

6α,9α-Difluoro-11β-hydroxy-16α,17α-isopropylidenedioxy-21-(2-oxo-tetrahydro-furan-3R-yl-sulfanyl)-pregna-1,4-diene-3,20-dione To a stirring solution of 6α,9α-difluoro-11β-hydroxy-21-mercapto-16α,17α-isopropylidenedioxy-pregna-1,4-diene-3,20-dione (100 mg, 0.21 mmol) and methanesulfonic acid 2-oxo-tetrahydrofuran -3S-yl ester (Intermediate 7, 38 mg, 0.21 mmol) in anhydrous DMF (2 ml) was added, in a single portion, potassium carbonate (15 mg, 0.11 mmol). The resulting reaction mixture was stirred under a nitrogen atmosphere for 1.5 h at which point another quantity of potassium carbonate (15 mg, 0.11 mmol) was added. The mixture was stirred for a further 2.5 h. Ethyl acetate (10 ml) and 2M hydrochloric acid (10 ml) were added and the organic phase was separated and washed with water (10 ml) and saturated brine (10 ml) then dried over anhydrous magnesium sulfate. Removal of the solvent under reduced pressure yielded a yellow residue which was purified by flash column chromatography on silica gel using diethyl ether as eluent. Removal of the solvent from appropriate fractions under reduced pressure gave the title compound as a white solid (91 mg, 77%); spectroscopic data were identical to those obtained for isomer B in Example 3.

EXAMPLE 6

6α,9α-Difluoro-11β-hydroxy-16α,17α-isopropylidenedioxy-21-(2-oxo-tetrahydro-furan-3-yl-sulfanyl)-pregn -4-ene-3,20-dione To a stirring suspension of sodium hydride (72 mg of 60% w/w dispersion in mineral oil, 1.80 mmol) in anhydrous tetrahydrofuran (1 ml) at 0° C. under a nitrogen atmosphere was added, dropwise, a solution of α-mercapto-γ-butyrolactone (213 mg, 1.80 mmol) in anhydrous tetrahydrofuran (2 ml). The resulting solution was stirred at 0° C. for 30 minutes by which time effervescence had ceased. A solution of 6α,9α-difluoro-11β-hydroxy-16α,17α-isopropylidenedioxy-21-methanesulfonyloxy-pregn-4-ene-3,20-dione (Intermediate 8, 800 mg, 1.50 mmol) in anhydrous tetrahydrofuran (10 ml) was added and the reaction mixture was stirred for a further 1 h at 0° C. The reaction mixture was poured into water (20 ml) and extracted with ethyl acetate (20 ml×4). The combined organic extracts were then washed with saturated brine (20 ml) and dried over anhydrous magnesium sulfate. Removal of the solvent under reduced pressure yielded a residue which was purified by preparative reverse phase HPLC (Dynamax 60 ÅC18, 25 cm×41 mm i.d.) eluting with 55% acetonitrile/water at 45 ml/min/min with detection at 230 nm. Appropriate fractions were combined and evaporated under reduced pressure to yield the title compound. isomer A (282 mg, 34%): mp 124–128° C.; MS (TSP+ve) m/z 555 (M+H)$^+$; IR $\nu_{max}$ (KBr) 3468, 1760, 1716,1669 cm$^{-1}$; NMR δ (DMSO-d$_6$) includes 5.80 (1H, s), 5.60 and 5.41 (1H, 2m), 5.30 (1H, bs), 4.90 (1H, bs), 4.40–4.10 (3H, m), 4.08–3.73 (3H, m), 1.47 (3H, s), 1.37 (3H, s), 1.08 (3H, s), 0.79 (3H, s). (Found: C, 59.67; H, 6.39; S, 5.57. C$_{28}$H$_{36}$F$_2$O$_7$S.0.5H$_2$O requires C, 59.67; H, 6.62; S, 5.69%) and title compound. isomer B (235 mg, 28%): mp 224–228° C.; MS (TSP+ve) m/z 555 (M+H)$^+$; IR $\nu_{max}$ (KBr) 3482, 1762, 1714, 1669 cm$^{-1}$; NMR δ (DMSO-d$_6$) includes 5.81 (1H, s), 5.60 and 5.41 (1H, 2m), 5.28 (1H, bs), 4.91 (1H, bs), 4.40–4.10 (4H, m), 3.95–3.73 (2H, m), 1.47 (3H. s), 1.38 (3H, s), 1.11 (3H,s) 0.77 (3H, s). (Found: C, 59.78; H, 6.57; S, 5.62. C$_{28}$H$_{36}$F$_2$O$_7$S.0.5H$_2$O requires C, 59.67; H. 6.62; S, 5.69%).

EXAMPLE 7

16α,17α-(R-Butylidenedioxy)-6α,9α-difluoro-11β-hydroxy-21-(2-oxo-tetrahydro-furan-3-yl-sulfanyl)-pregna-1,4-diene-3,20-dione To a stirring suspension of sodium hydride (49 mg of 60% w/w dispersion in mineral oil, 1.22 mmol) in anhydrous tetrahydrofuran (2 ml) at 0° C. under a nitrogen atmosphere was added, dropwise, a solution of α-mercapto-γ-butyrolactone (144 mg, 1.22 mmol) in anhydrous tetrahydrofuran (4 ml). The resulting solution was stirred at 0° C. for 30 minutes by which time effervescence had ceased. A solution of 16α,17α-(R-butylidenedioxy)-6α,9α-difluoro-11β-hydroxy-21-methanesulfonyloxy-pregna-1,4-diene-3,20-dione (Intermediate 9, 557 mg, 1.02 mmol) in anhydrous tetrahydrofuran (15 ml) was added and the reaction mixture was stirred for 18 h at 0–21 °C. Further quantities of sodium hydride (24 mg of 60% w/w dispersion in mineral oil, 0.61 mmol) and α-mercapto-γ-butyrolactone (72 mg, 0.61 mmol) were added and the mixture stirred for another 1 h. The reaction mixture was poured into water (30 ml) and extracted with ethyl acetate (30 ml×2). The combined organic extracts were then washed with saturated brine (30 ml) and dried over anhydrous magnesium sulfate. Removal of the solvent under reduced pressure yielded a yellow residue which was purified by preparative reverse phase HPLC (Dynamax 60 ÅC18, 25 cm×41 mm i.d.) eluting with 60% acetonitrile/water at 45 m/min with detection at 230 nm. Appropriate fractions were combined and evaporated under reduced pressure to yield the title compound. isomer A (152 mg, 26%): mp 221–223° C.; MS (TSP+ve) m/z 567 (M+H)$^+$; IR ν$_{max}$ (KBr) 3356, 1766, 1715, 1665, 1607 cm$^{-1}$; NMR δ (CDCl$_3$) includes 7.12 (1H, d, J 10 Hz), 6.44 (1H, s), 6.38 (1H, d, J 10 Hz), 5.48 and 5.28 (1H, 2m), 4.93 (1H, d, J 5.5 Hz), 4.62 (1H, t, J 4.5 Hz), 4.55–4.32 (3H, m), 4.05 (1H, d, J 19 Hz), 3.71 (1H, d, J 19 Hz), 3.78 (1H, m), 1.52 (3H, s), 0.95 (3H, s), 0.92 (3H, t, J 7.5 Hz). (Found: C, 61.02; H, 6.57; S, 5.28. C$_{29}$H$_{36}$F$_2$O$_7$S.0.2H$_2$O requires C, 61.08; H, 6.43; S, 5.62%) and title compound. isomer B (92 mg, 16%): mp 219–221° C.; MS (TSP+ve) m/z 567 (M+H)$^+$; IR ν$_{max}$ (KBr) 3356, 1768, 1721, 1665, 1625, 1609 cm$^{-1}$; NMR δ (CDCl$_3$) includes 7.12 (1H, d, J 10 Hz), 6.44 (1H s), 6.40 (1H, d, J 10 Hz), 5.48 and 5.29 (1H, 2m), 4.92 (1H, d, J 5 Hz), 4.67 (1H, t, J 4.5 Hz), 4.55 –4.30 (3H, m). 4.19 (1H, d, J 18 Hz), 3.81 (1H, d, J 18 Hz), 3.68 (1H, m), 1.53 (3H s), 0.92 (3H, s), 0.92 (3H, t, J 7.5 Hz). (Found: C, 61.35; H. 6.39; S, 5.57. C$_{29}$H$_{36}$F$_2$O$_7$S requires C, 61.47; H, 6.40; S, 5.66%).

EXAMPLE 8

16α,17α-(R-Butylidenedioxy)-6α,9α-difluoro-11β-hydroxy-21-(2-oxo-tetrahydro-furan-3-yl-sulfanyl)-pregn-4-ene-3,20-dione To a stirring suspension of sodium hydride (63 mg of 60% w/w dispersion in mineral oil, 1.58 mmol) in anhydrous tetrahydrofuran (1 ml) at 0° C. under a nitrogen atmosphere was added, dropwise, a solution of α-mercapto-γ-butyrolactone (187 mg, 1.58 mmol) in anhydrous tetrahydrofuran (2 ml). The resulting solution was stirred at 0° C. for 45 minutes by which time effervescence had ceased. A solution of 16α,17α-(R-butylidenedioxy)-6α,9α-difluoro-11β-hydroxy-21-methanesulfonyloxy-pregn-4-ene-3,20-dione (Intermediate 10, 722 mg, 1.32 mmol) in anhydrous tetrahydrofuran (10 ml) was added and the reaction mixture was stirred for a further 1.5 h at 0–21° C. The reaction mixture was poured into water (30 ml) and extracted with ethyl acetate (30 ml×2). The combined organic extracts were then washed with saturated brine (30 ml) and dried over anhydrous magnesium sulfate. Removal of the solvent under reduced pressure yielded a white solid which was purified by preparative reverse phase HPLC (Dynamax 60 ÅC18, 25 cm×41 mm i.d.) eluting with 60% acetonitrile/water at 45 ml/min with detection at 230 nm. Appropriate fractions were combined and evaporated under reduced pressure to yield the title compound. isomer A (335 mg, 45%): mp 159–161° C.; MS (TSP+ve) m/z 569 (M+H)$^+$; IR ν$_{max}$ (KBr) 1761, 1714, 1668 cm$^{-1}$; NMR δ (CDCl$_3$) includes 6.14 (3H, s), 5.37 and 5.17 (1H, 2m). 4.95 (1H, d, J 5 Hz), 4.63 (1H, t, J 4.5 Hz), 4.55–4.29 (3H, m), 4.08 (1H, d, J 18 Hz), 3.72 (1H, d, J 18 Hz), 3.77 (1H, m), 1.52 (3H, s), 0.95 (3H, t, J 5 Hz), 0.92 (3H, s). (Found: C, 60.31; H, 6.86; S, 5.52. C$_{29}$H$_{38}$F$_2$O$_7$S.0.4H$_2$O requires C, 60.48; H, 6.79; S 5.57%) and title compound. isomer B (137 mg, 18%): mp 99–102° C.; MS (TSP+ve) m/z 569 (M+H)$^+$; IR ν$_{max}$ (KBr) 1760, 1714, 1668 cm$^{-1}$; NMR δ (CDCl$_3$) includes 6.14 (1H, s), 5.37 and 5.18 (1H, 2m). 4.92 (1H, d, J 5 Hz), 4.69 (1H, t, J 4.5 Hz), 4.54–4.30 (3H, m), 4.22 (1H, d, J 18 Hz), 3.80 (1H, d, J 18 Hz), 3.70 (1H, m), 1.52 (3H, s), 0.95 (3H, t, J 7.5 Hz), 0.90 (3H, s). (Found: C, 59.47; H, 6.64; S, 5.41. C$_{29}$H$_{38}$F$_2$O$_7$S.0.8H$_2$O requires C, 59.74; H, 6.85; S, 5.50%).

EXAMPLE 9

16α,17α-Butylidenedioxy-11β-hydroxy-21-(2-oxo-tetrahydrofuran-3-yl-sulfanyl)-pregna-1,4-diene-3,20-dione To a stirring solution of 16α,17α-butylidenedioxy-11β-hydroxy-21-mercapto-pregna-1,4-diene-3,20-dione (135 mg, 0.30 mmol) in dichloromethane (3 ml) under a nitrogen atmosphere was added triethylamine (126 μl, 0.91 mmol). The suspension was then cooled to 0° C. and α-bromo-γ-butyrolactone (75 μl, 0.91 mmol) was added. The resulting reaction mixture was then stirred at 0–21° C. for 4 h. The solvent was removed from the mixture under reduced pressure and the residue was separated between ethyl acetate (50 ml) and 0.5 M hydrochloric acid (50 ml). The organic layer was washed with water (50 ml×2) and saturated brine (50 ml×2) and was then dried over anhydrous magnesium sulfate. Removal of the solvent under reduced pressure yielded a colourless residue which was purified by reverse phase HPLC (Dynamax 60 ÅC18, 25 cm×41 mm i.d) eluting with 50–95% acetonitrile/water at 45 ml/min with detection at 230 nm. Appropriate fractions were combined and evaporated under reduced pressure to yield the title compound. diastereoisomeric mixture A (69 mg, 43%): MS (TSP+ve) m/z 531 (M+H)$^+$; IR ν$_{max}$ (KBr) 1761, 1714, 1659, 1619, 1602 cm$^{-1}$; NMR δ (CDCl$_3$) includes 7.26 (1H, d, J 10 Hz), 6.28 (1H, d, J 10 Hz), 6.03 (1H ,s), 5.20 and 4.92 (1H, 2 d, J 4 Hz), 5.18 and 4.60 (1H, 2t, J 4.5 Hz), 4.55–4.30 (3H, m), 4.09–3.65 (3H, m), 1.46 (3H, s), 0.99 and 0.95 (3H, 2s), 0.92 and 0.91 (3H, 2t, J 7.5 Hz). (Found: C, 64.97; H, 7.64; S, 5.62. C$_{29}$H$_{38}$O$_7$S.0.3H$_2$O.0.4C$_4$H$_{10}$O requires C, 64.97; H. 7.59; S, 5.67%) and title compound. diastereoisomeric mixture B (73 mg, 46%): mp 150–154° C.; MS (TSP+ve) m/z 531 (M+H)$^+$; IR ν$_{max}$ (KBr) 1764, 1714, 1659, 1618 cm$^{-1}$; NMR δ (CDCl$_3$) includes 7.25 (1H, d, J 10 Hz), 6.28 (1H, d, J 10 Hz), 6.03 (1H, s), 5.18 and 4.91 (1H, 2d, J 5 Hz), 5.19 and 4.64 (1H, 2t, J 4.5 Hz), 4.55–4.13 (4H, m), 3.83–3.66 (2H, m), 1.46 (3H, s), 0.98 and 0.93 (3H, 2s), 0.93 (3H, m). (Found: C, 65.42; H, 7.49; S, 5.75. $C_{29}H_{38}O_7S$ requires C, 65.64; H. 7.22; S, 6.04%).

EXAMPLE 10

6α,9α-Difluoro-11β-hydroxy-16α,17α-isopropylidenedioxy-21-(2-oxo-tetrahydro-furan4-yl-sulfanyl)-pregna-1,4-diene-3,20-dione Method 1

A suspension of 6α,9α-difluoro-11β-hydroxy-21-mercapto-16α,17α-isopropylidenedioxy-1,4-diene-3,20-pregna-dione (100 mg, 0.23 mmol) and anhydrous potassium carbonate (32 mg, 0.23 mmol) in dry DMF (2 ml) was treated with 2(5H)-furanone (0.035 ml, 0.5 mmol) and the mixture was stirred at 20° C. under a nitrogen atmosphere for 4 h. The reaction mixture was poured into 0.5 M hydrochloric acid (20 ml) and extracted with ethyl acetate (40 ml). The organic phase was washed with water (10 ml), aqueous sodium bicarbonate solution (20 ml), water, saturated brine (20 ml each) and dried over anhydrous magnesium sulfate. Removal of the solvent under reduced pressure and trituration in diethyl ether (3×2 ml) yielded the title compound (100 mg, 79%): MS (ES+ve) m/z 553 (M+H)$^+$; IR $v_{max}$ (KBr) 1780, 1715, 1668 cm$^{-1}$; NMR δ (DMSO-d$_6$) includes 7.30 (1H, d, J 9 Hz), 6.31 (1H, d, J 9 Hz). 6.13 (1H, s), 5.70 and 5.58 (1H, 2 m), 5.51 (1H, d, J 4 Hz), 4.93 (1H, d, J 4 Hz), 4.58 (1H, dd, J 9 and 8 Hz), 4.23 (2H, m), 4.03 and 4.01 (1H, 2d, J 17 Hz), 3.68 and 3.66 (1H, 2d, J 17 Hz), 3.90 (1H, m), 3.83 (1H, d, J 17.5 Hz). 3.02 (1H, dd, J 8 and 2 Hz), 1.51 (3H, s), 1.37 (3H, s), 1.11 (3H, s), 0.83 (3H. s); NMR δ (DMSO-d$_6$) includes 206.2,184.2, 175.4 (3 C=O) (Found: C, 59.31: H, 6.37; N, 0.60; S, 5.01. $C_{28}H_{34}F_2O_7S.0.25C_3H_7NO.0.6H_2O$ requires C. 59.36; H, 6.40; N, 0.60; S 5.51%).

Method 2

A solution of 6α,9α-difluoro-11β-hydroxy-16α,17α-isopropylidenedioxy-21-trifluoromethanesulfonyloxy-pregna-1,4-diene-3,20-dione (Intermediate 11, 100 mg, 0.17 mmol) and α-mercapto-γ-butyrolactone (20 mg, 0.17 mmol) in anhydrous tetrahydrofuran (5 ml) was treated with triethylamine (0.024 ml. 0.17 mmol) and the mixture was stirred at 20° C. under a nitrogen atmosphere for 24 h and then at 75° C. for 24 h. Removal of the solvent under reduced pressure yielded a yellow foam. The crude product was purified by column chromatography on silica gel using ethyl acetate-cyclohexane (2:3) as eluent. Removal of the solvent from the required fractions gave the title compound (20 mg, 21%): NMR δ (CDCl$_3$) includes 7.13 (1H, d, J 10 Hz), 6.44 (1H, s), 6.38 (1H, d, J 10 Hz), 5.50 and 5.30 (1H, 2m), 5.03 (1H, d, J 5 Hz), 4.64 (1H, m), 4.42 (1H, m), 4.24 (1H, m), 3.87 (1H, m), 3.71 and 3.68 (1H, 2d, J 17 Hz) 3.57 and 3.53 (1H, 2d, J 16 Hz), 2.96 (1H, m), 1.53 (3H, s), 1.43 (3H, s), 1.15 (3H, s), 0.93 (3H, s).

EXAMPLE 11

16α,17α-(R-Butylidenedioxy)-6α,9α-difluoro-11β-hydroxy-21-(2-oxo-tetrahydro-furan-4-yl-sulfanyl)-pregn-4-ene-3,20-dione A solution of 16α,17α-(R-butylidenedioxy)-6α,9α-difluoro-11β-hydroxy-21-mercapto-pregn-4-ene-3,20-dione (Intermediate 13, 500 mg, 1.03 mmol) and 2(5H)-furanone (0.073 ml, 1.03 mmol) in anhydrous tetrahydrofuran (10 ml) was treated with triethylamine (0.14 ml, 1.03 mmol) and the mixture was stirred at 20° C. under a nitrogen atmosphere for 48 h. Removal of the solvent under reduced pressure yielded a cream foam. The crude product was purified by column chromatography on silica gel using ethyl acetate-cyclohexane (3:2) as eluent, isolating the title compound (413 mg, 71%): MS (TSP+ve) m/z 569 (M+H)$^+$; IR $v_{max}$ (KBr) 1779, 1712, 1668 cm$^{-1}$; NMR δ (CDCl$_3$) includes 6.16 (1H, s), 5.37 and 5.18 (1H, 2m), 4.91 (1H, d, J 5 Hz), 4.70 (1H, t, J 4 Hz), 4.62 (1H, dd, J 9 and 7 Hz), 4.40 (1H, m), 4.22 (1H, m), 3.82 (1H, m), 3.63 and 3.60 (1H, 2 d, J 14 Hz), 3.43 and 3.39 (1H, 2 d, J 16 Hz), 2.95 (1H, dd, J 18 and 8 Hz), 1.52 (3H, s), 0.94 (3H, t, J 7 Hz), 0.91 (3H, s). (Found: C, 62.39; H, 7.41; S, 5.04. $C_{29}H_{38}F_2O_7S$. 0.3 $C_6H_{12}$ requires C, 62.29; H, 7.06; S 5.40%).

EXAMPLE 12

6α,9α-Difluoro-11β-hydroxy-16α,17α-isopropylidenedioxy-21-(2-oxo-tetrahydro-furan-5-yl-sulfanyl)-pregna-1,4-diene-3,20-dione A solution of 6α,9α-difluoro-11β-hydroxy-21-mercapto-16α,17α-isopropylidenedioxy-pregna-1,4-diene-3,20-dione (400 mg, 0.85 mmol) and γ-chloro-γ-butyrolactone (103 mg, 0.85 mmol) in anhydrous tetrahydrofuran (10 ml) was treated with triethylamine (0.12 ml, 0.85 mmol) and the mixture was stirred at 20° C. under a nitrogen atmosphere for 24 h. Removal of the solvent under reduced pressure yielded a brown foam. The crude product was purified by column chromatography on silica gel using dichloromethane-ethyl acetate (3:1) as eluent. Removal of the solvent from appropriate fractions under reduced pressure gave the title compound isomer A (124 mg, 26%): mp 238–239° C.; MS (TSP+ve) m/z 553 (M+H)$^+$; IR $v_{max}$ (KBr) 1781, 1719,1669 cm$^{-1}$; NMR δ (CDCl$_3$) includes 7.19 (1H, d, J 10 Hz), 6.43 (1H, s), 6.37 (1H, d, J 10 Hz), 5.87 (1H, m), 5.49 and 5.29 (1H, 2 m), 5.02 (1H, d, J 4 Hz), 4.42 (1H, m), 3.92 (1H, d, J 17 Hz), 3.78 (1H, d, J 17 Hz), 1.53 (3H, s), 1.42 (3H, s), 1.17 (3H, s), 0.89 (3H, s). (Found: C, 59.55; H, 6.16; S, 5.58.$C_{28}H_{34}F_2O_7S.0.2CH_2Cl_2$ requires C, 59.46; H, 6.09; S, 5.63%) and the title compound, isomer B (62 mg, 13%): mp 244–246° C.; MS (TSP+ve) m/z 553 (M+H)$^+$; IR $v_{max}$ (KBr) 1784, 1715, 1688 cm$^{-1}$; NMR δ (CDCl$_3$) includes 7.14 (1H, d, J 10 Hz), 6.43 (1H, s), 6.38 (1H, d, J 10 Hz), 5.92 (1H, m), 5.49 and 5.29 (1H, 2 m), 5.06 (1H, d, J 4 Hz), 4.42 (1H, m), 3.91 (1H, d, J 18 Hz), 3.72 (1H, d, J 18 Hz), 1.52 (3H, s), 1.42 (3H, s), 1.17 (3H, s), 0.89 (3H, s). (Found: C, 60.98; H, 6.18; S, 5.63. $C_{28}H_{34}F_2O_7S$ requires C, 60.86; H, 6.20; S, 5.80%)

EXAMPLE 13

9α-Fluoro-11β-hydroxy-16α,17α-isopropylidenedioxy-21-(2-oxo-tetrahydro-furan-3-yl-sulfanyl)-pregna-1,4-diene-3,20-dione A solution of α-mercapto-γ-butyrolactone (254 mg, 2.15 mmol) in anhydrous tetrahydrofuran (4 ml) was added, dropwise, to a stirring suspension of sodium hydride (87 mg of 60% w/w dispersion in mineral oil, 2.15 mmol) in anhydrous tetrahydrofuran (4 ml) at 0° C. under a nitrogen atmosphere The resulting solution was stirred at 0° C. for 30 minutes and then a solution of 9α-fluoro-11β-hydroxy-16α,17α-isopropylidenedioxy-21-methanesulfonyloxy-pregna-1,4diene-3,20-dione (1.0 g, 1.95 mmol) in anhydrous DMF (2 ml) and tetrahydrofuran (8 ml) was added. After 6 h further quantities of α-mercapto-γ-butyrolactone (23 mg, 0.19 mmol) in anhydrous tetrahydrofuran (1 ml) and sodium hydride (8 mg of 60% w/w dispersion in mineral oil, 0.19 mmol) were added and the reaction mixture was stirred for a further 16 h at 21° C. The reaction mixture was poured into water (40 ml) and extracted with ethyl acetate (40 ml×2). The combined organic extracts were washed with saturated brine (20 ml) and dried over anhydrous magnesium sulfate. Removal of the solvent under reduced pressure yielded a light brown solid which was triturated in ethyl acetate (20 ml) for 20 min and then filtered. The solid obtained was purified by preparative reverse phase HPLC (Dynamax 60 ÅC18, 25 cm×41 mm i.d.) eluting with 50% acetonitrile/water at 45 ml/min with detection at 235 nm. Appropriate fractions were combined and evaporated under reduced pressure to yield the tie compound, isomer A (87.6 mg, 28%): mp 230–233° C.; MS (TSP+ve) m/z 535 (M+H)$^+$; IR $v_{max}$ (KBr) 1760, 1719, 1663 cm$^{-1}$; NMR δ (CDCl$_3$) includes 7.21 (1H, d, J 10 Hz), 6.35 (1H, d, J 10 Hz), 6.13 (1H, s), 5.06 (1H, d, J 4.5 Hz), 4.534.33 (3H, m), 4.04 (1H, d, J 18.5 Hz), 3.89 (1H, d, J 18.5 Hz), 3.81 (1H, dd, J 8.5 and 3.5 Hz), 1.54 (3H, s), 1.42 (3H, s), 1.16 (3H, s), 0.94 (3H s).

The filtrate from the trituration was evaporated under reduced pressure to give a light brown solid which was subjected to preparative reverse phase HPLC (Dynamax 60 ÅC18, 25 cm×41 mm i.d.) eluting with 50% acetonitrile/water at 45 ml/min with detection at 235 nm. Appropriate fractions were combined and evaporated under reduced pressure to yield a white solid which was purified by column chromatography on silica gel using dichloromethane-ethyl acetate (2:1) as eluent. Removal of the solvent from the required fractions gave the title compound, isomer B (72 mg, 23%): mp 241–243° C.; MS (ES+ve) m/z 535 (M+H)$^+$; IR $v_{max}$ (KBr) 1766, 1712, 1663 cm$^{-1}$; NMR δ (CDCl$_3$) includes 7.20 (1H, d, J 10 Hz). 6.35 (1H, d, J 10 Hz), 6.13 (1H, s), 5.04 (1H, d, J 5 Hz), 4.53–4.32 (3H, m). 4.28 (1H, d, J 17.5 Hz), 3.88 (1H, d, J 18 Hz), 3.70 (1H, dd, J 8.5 and 4.5 Hz). 1.54 (3H, s), 1.42 (3H,s), 1.18 (3H, s), 0.91 (3H, s).

EXAMPLE 14

9α-Fluoro-11β-hydroxy-16β-methyl-21-(2-oxo-tetrahydro-furan-3-yl-sulfanyl)-17α-propionyloxy-pregna-1,4-diene-3,20-dione To a stirring solution of 9α-fluoro-11β-hydroxy-21-methanesulfonyloxy-16β-methyl-17α-propionyloxy-pregna-1,4-diene-3,20-dione (500 mg, 0.95 mmol) and α-mercapto-γ-butyrolactone (168 mg, 1.42 mmol) in anhydrous DMF (5 ml) under a nitrogen atmosphere was added, triethylamine (198 μl, 1.42 mmol). The resulting reaction mixture was stirred at room temperature for 90 h. The reaction mixture was then poured into water (100 ml) and the precipitated solid collected by filtration. The solid was washed with water (3×25 ml) then dissolved in ethyl acetate (75 ml). The resulting solution was washed with 1N hydrochloric acid (25 ml), water (25 ml), saturated sodium bicarbonate solution (25 ml), water (25 ml) and finally saturated brine (2×25 ml). It was then dried over anhydrous magnesium sulfate and the solvent was removed under reduced pressure to yield a pale yellow foam. This material was purified by column chromatography eluting with ethyl acetate-40–60 petroleum ether (3:2) Appropriate fractions were combined and evaporated under reduced pressure to yield a white solid, the title compound. (381 mg, 73%): MS (ES+ve) m/z 549 (M+H)$^+$; NMR δ (CDCl$_3$) includes 7.21 (1H, dd, J 10 and 4 Hz), 6.35 (1H, dd, J 10 and 2 Hz), 6.14 (1H. bs), 4.52–4.26 (3H, m), 3.92 (0.5H, d, J 17 Hz), 3.87 (0.5H, dd, J 9 and 4 Hz). 3.78 (0.5H, d, J 18 Hz), 3.64 (0.5H, dd, J 9 and 5.5 Hz), 3.45 (0.5H, d, J 17 Hz), 3.32 (0.5H, d, J 18 Hz), 2.37 (2H, q, J 7.5 Hz), 1.56 (3H, s), 1.40 (3H, d. J 7 Hz), 1.14 (3H, t, J 7.5 Hz), 1.00 (1.5H, s), 0.97 (1.5H, s).

Pharmacological Activity
In Vitro

The pharmacological activity was studied in a functional in vitro assay to demonstrate glucocorticoid activity which is generally predictive of anti-inflammatory or anti-allergic activity in-vivo.

The functional assay used was a modification of the method described by T. S Berger et al, of J. of Steroid Biochem. Molec. Biol. 1992, 41 (3–8), 733–738, "Interaction of Glucocorticoid analogues with the Human Glucocorticoid Receptor".

Thus, Hela cells were stably transfected with a detectable reporter gene (secreted placental alkaline phosphatase, sPAP) under the control of a glucocorticoid response promoter (the LTR of the mouse mammary tumour virus, MMTV). Various concentrations of standard (dexamethasone) or compounds of the invention were incubated with transfected Hela cells for 72 hours. At the end of the incubation, substrate (p-nitrophenol acetate) for sPAP was added and the product measured by a spectrophotometric method. Increased absorbance reflected increased sPAP transcription and concentration-response lines were constructed such that $EC_{50}$-values could be estimated.

In this test, the isomers of Examples 3, 6, 7 and 8, isomer A of Example 9 and the compounds of Examples 1, 2, 10 and 11 had $EC_{50}$-values of less than 600 nM.

Hydrolysis in Blood

All the isomers of the Examples were unstable in human plasma (half-lives less than 60 min), indicating that they are expected to possess an advantageous in vivo side effect profile.

In Vivo (i) Anti-inflammatory Activity—Inhibition of lung eosinophilia in Brown Norway rats Male Brown norway rats (150–180 g) are sensitised with 1 ml intra-peritoneally (ip) containing 10 mg Al (OH)$_3$ +1 mg Ovalbumin (OVA) on day 1. On day 7 each rat received 1 ml ip containing 10 mg Al(OH)$_3$ +100 ug OVA. On day 14, each rat received an intratracheal (IT) dose of compound or vehicle (0.2 ml), under isoflurane anaesthesia. Compounds are suspended in 0.9% saline/0.2% Tween 80. 4 h after compound administration, each animal receives 400 ug OVA in saline IT (0.2 ml). On day 16, animals are killed and the lungs lavaged with 5 mls of lavage fluid (10 mM EDTA, phosphate buffered saline (pH 7.4), 5 units heparin/ml, 0.1% BSA). The samples are centrifuged at 1000 RPM for 10 minutes. The supernatant is removed and the cells resuspended in 0.5 ml lavage fluid. Total cells are counted with a Sysmex counter. Cytospin slides are prepared using 75 ul of the cell suspension and the cells are stained with May-Grunwald stain. Differential cell counts are performed using a microscope. Numbers of eosinophils are calculated per ul of lavage fluid per rat allowing percentage reduction in eosinophilia to be calculated.

| Compound | Dose | % Reduction in Eosinophilia |
| --- | --- | --- |
| Budesonide | 250 μg | 82 |
| Example 3 Isomer A | 250 μg | 74 |
| Example 3 Isomer A | 750 μg | 97 |

(II) Systemic Effects—ACTH Suppression in Adrenalectomised Rats

Male CD rats (90–120 g) were adrenalectomised under Isoflurane anaesthesia and drinking water was supplemented with 0.9% saline. Four days later the animals receive a single intravenous dose of compound dissolved in DMA/PEG-200/ distilled water (1:6:3) (0.2 ml) at 10 am. At 2 h and 4 h afterwards animals are sacrificed by administration of Euthetal and blood samples are taken by intra-cardiac puncture and collected into heparinised tubes. The samples are centrifuged (20 minutes at 1000 RPM at 4 deg C), the plasma is collected and assayed by Radioimmunoassay (RIA) for Adrenocorticotrophic hormone (ACTH) using a DPC double antibody RIA kit. Intact and vehicle control groups for each time point assessed were included in each experiment in order to account for diurnal variation in ACTH and effects of vehicle. Results are calculated with respect to the RIA standard curve and expressed as ACTH pg/ml plasma, allowing percentage reduction in ACTH to be calculated.

|  |  | % Reduction in ACTH | |
| --- | --- | --- | --- |
| Compound | Dose | at 2 h | at 4 h |
| Budesonide | 6.25 µg | 61 | 32 |
| Example 3 Isomer A | 500 µg | 16 | 15 |

This result illustrates the minimal systemic activity associated with these plasma labile derivatives.

Pharmaceutical Formulations

The following are examples of suitable formulations of compounds of the invention. The term "active ingredient" is used herein to represent a compound of the invention and can be, for example, the isomers (or a mixture thereof) of Examples 1, 4, 6, 8, 10 or 11.

1. Inhalation Cartridges

| Active ingredient micronised | 1.6% w/w |
| --- | --- |
| Lactose BP | 98.4% w/w. |

The active ingredient is micronised in a conventional manner to a fine particle size range such as to permit inhalation of substantially all of the medicament into the lungs upon administration, prior to blending with normal tableting grade lactose in a high energy mixer. The powder blend is filled into gelatin capsules on a suitable encapsulating machine. The contents of the cartridges are administered using a powder inhaler such as ROTAHALER™ inhaler. Alternatively, the powder blend can be filled into blisters of a blister pack or strip. The contents of the blister pack or strip are administered using a powder inhaler such as DISKHALER™ or DISKUS™ inhaler.

2. Aerosol Formulation (i) Suspension

|  | mg/actuation | per can |
| --- | --- | --- |
| Active ingredient micronised | 0.25 | 40 mg |
| 1,1,1,2-tetrafluoroethane | 74.75 | 11.96 g |

The active ingredient is weighed directly into an open aluminium can and a metering valve is then crimped in place. 1,1,1,2-Tetrafluoroethane is then added to the can under pressure through the valve and the can shaken to disperse the drug. The resultant inhaler contains 0.33% w/w active ingredient.

(ii) Solution

|  | mg/actuation | per can |
| --- | --- | --- |
| Active ingredient micronised | 0.25 | 40 mg |
| Ethanol (anhydrous) | 7.5 | 1.2 g |
| 1,1,1,2-tetrafluoroethane | 67.25 | 10.76 g |

Active ingredient is dissolved in the ethanol. The resultant ethanolic solution of active ingredient is metered into an open aluminium can and a metering valve is then crimped in place. 1,1,1,2-Tetrafluoroethane is then added under pressure through the valve. The resultant inhaler contains 0.33% w/w active ingredient and 10% w/w ethanol.

3. Cream

|  | % w/w |
| --- | --- |
| Active ingredient micronised | 0.2 |
| Liquid Paraffin | 40 |
| Cetostearyl alcohol | 5 |
| Cetomacrogol 1000 | 1 |
| Isopropylmyristate | 5 |
| Propylene glycol | 10 |
| Benzoic acid | 0.2 |
| Sodium phosphate | 0.05 |
| Citric acid/monohydrate | 0.05 |
| Purified water to | 100 |

The micronised active ingredient is dispersed in a portion of the water containing a portion of the cetomacrogol 1000. The liquid paraffin, cetostearyl alcohol and isopropyl myristate are melted together, cooled to 50 to 60° C. and added to the remaining water containing the propylene glycol, benzoic acid (preservative), and sodium phosphate and citric acid (buffering agents). The resultant oil phase is added to the active ingredient suspension with stirring until cool.

Protection may be sought for any subject matter described herein. Thus, protection may be sought for the compounds (including intermediates), compositions, processes and uses described herein.

We claim:

1. A compound of formula (I)

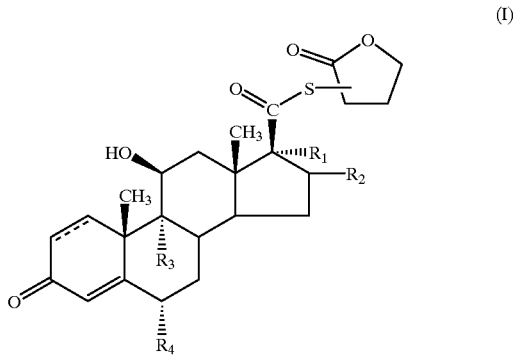

and solvates thereof, in which $R_1$ individually represents —OC(=O)$C_{1-6}$ alkyl;

$R_2$ individually represents hydrogen, methyl which may be in the α or β configuration or methylene;

or R1 and R₂ together represent

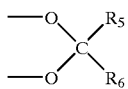

wherein
R₅ and R₆ are the same or different and each represents hydrogen or $C_{1-6}$ alkyl;
R₃ and R₄ are the same or different and each represents hydrogen or halogen; and
═══ represents a single or double bond.

2. A compound according to claim 1 in which R₁ individually represents OC(═O)$C_{1-3}$alkyl.

3. A compound according to claim 1 or claim 2 in which R₁ represents OC═(O)ethyl.

4. A compound according to claim 1 in which R₁ represents OC(═O)ethyl.

5. A compound according to claim 1 in which R₂ is methyl.

6. A compound according to claim 1 in which R₁ and R₂ together represent

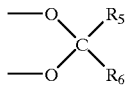

wherein R₅ and R₆ are the same or different and each represents hydrogen or $C_{1-6}$ alkyl.

7. A compound according to claim 6 in which R₅ and R₆ are the same or different and each represents hydrogen or $C_{1-3}$alkyl.

8. A compound according to claim 6 in which R₅ and R₆ are the same or different and each represents hydrogen, methyl or n-propyl.

9. A compound according to claim 6 in which R₅ and R₆ are both methyl.

10. A compound according to claim 6 in which R₅ and R₆ are different and each represents hydrogen or n-propyl.

11. A compound according to claim 1 in which R₃ and R₄ are the same or different and each represents hydrogen, fluorine or chlorine.

12. A compound according to claim 1 in which R₃ and R₄ are the same or different and each represents hydrogen or fluorine.

13. A compound according to claim 1 in which R₃ and R₄ are both fluorine.

14. A compound according to claim 1 in which R₁ individually represents OC(═O) $C_{1-6}$alkyl; R₂ is methyl; R₃ and R₄ are the same or different and each represents hydrogen or fluorine; and ═══ represents a single or a double bond.

15. A compound according to claim 14 in which R₁ individually represents OC(═O) ethyl and R₃ and R₄ are both fluorine.

16. A compound according to claim 1 in which R₁ and R₂ together represent

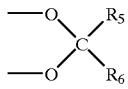

wherein R₅ and R₆ are the same or different and each represents hydrogen or $C_{1-6}$alkyl; R₃ and R₄ are the same or different and each represents hydrogen or fluorine; and
═══ represents a single or a double bond.

17. A compound according to claim 15 in which R₅ and R₆ are the same or different and each represents hydrogen, methyl or n-propyl and R₃ and R₄ are both fluorine.

18. A compound according to claim 1 in which S is bonded to the alpha carbon atom of the lactone moiety.

19. A compound according to claim 1 in which S is bonded to the beta carbon atom of the lactone moiety.

20. 6α,9α-Difluoro-11β-hydroxy-16α-methyl-21-(2-oxo-tetrahydro-furan-3-yl-sulfanyl)-17α-propionyloxy-pregn-4-ene-3,20-dione;
16α,17α-(R-Butylidenedioxy)-6α,9α-difluoro-11β-hydroxy-21-(2-oxo-tetrahydro-furan-3-yl-sulfanyl)-pregna-1,4-diene-3,20-dione;
16α,17α-Butylidenedioxy-11β-hydroxy-21-(2-oxo-tetrahydrofuran-3-yl-sulfanyl)-pregna-1,4-diene-3,20-dione;
6α,9α-Difluoro-11β-hydroxy-16α,17α-isopropylidenedioxy-21-(2-oxo-tetrahydro-furan-5-yl-sulfanyl)-pregna-1,4-diene-3,20-dione;
9α-Fluoro-11β-hydroxy-16α,17α-isopropylidenedioxy-21-(2-oxo-tetrahydro-furan-3-yl-sulfanyl)-pregna-1,4-diene-3,20-dione;
9α-Fluoro-11β-hydroxy-16β-methyl-21-(2-oxo-tetrahydro-furan-3-yl-sulfanyl)-17α-propionyloxy-pregna-1,4-diene-3,20-dione;
and solvates thereof.

21. 6α,9α-Difluoro-11β-hydroxy-16α-methyl-21-(2-oxo-tetrahydro-furan-3-yl-sulfanyl)-17α-propionyloxy-pregna-1,4-diene-3,20-dione;
and solvates thereof.

22. 6α,9α-Difluoro-11β-hydroxy-16α,17α-isopropylidenedioxy-21-(2-oxo-tetrahydro-furan-3-yl-sulfanyl)-pregna-1,4-diene-3,20-dione;
and solvates thereof.

23. 6α,9α-Difluoro-11β-hydroxy-16α,17α-isopropylidenedioxy-21-(2-oxo-tetrahydro-furan-3-yl-sulfanyl)-pregn-4-ene-3,20-dione;
and solvates thereof.

24. 6α,9α-Difluoro-11β-hydroxy-16α,17α-isopropylidenedioxy-21-(2-oxo-tetrahydro-furan-4-yl-sulfanyl)-pregna-1,4-diene-3,20-dione;
and solvates thereof.

25. 16α,17α-(R-Butylidenedioxy)6α,9α-difluoro-11β-hydroxy-21-(2-oxo-tetrahydro-furan-4-yl-sulfanyl)-pregn-4-ene-3,20-dione;
and solvates thereof.

26. 16α,17α-(R-Butylidenedioxy)-6α,9α-difluoro-11β-hydroxy-21-(2-oxo-tetrahydro-furan-3-yl-sulfanyl)-pregn-4-ene-3,20-dione;
and solvates thereof.

27. A pharmaceutical composition comprising a compound of formula (I) as defined in claim 1 or a physiologically acceptable solvate thereof, together, in admixture with one or more physiologically acceptable diluents or carriers.

28. A pharmaceutical aerosol formulation comprising a compound of formula (I) as defined in claim 1 or a physiologically acceptable solvate thereof and a fluorocarbon or hydrogen-containing chlorofluorocarbon as propellant, optionally in combination with a surfactant and/or a co-solvent.

29. A composition comprising a compound of formula (I) as defined in claim 1 or a physiologically acceptable solvate thereof and another therapeutically active agent.

30. A composition according to claim 29 in which said another therapeutically active agent is a $β_2$-adrenoreceptor agonist.

31. A method for the treatment of a human or animal subject with an inflammatory and/or allergic disorder, which method comprises administering to said human or animal subject an effective amount of a compound of formula (I) as defined in claim 1 or a physiologically acceptable solvate thereof.

32. A process for preparing a compound of formula (I) as claimed in claim 1, comprising:

A. reacting a compound of formula (II)

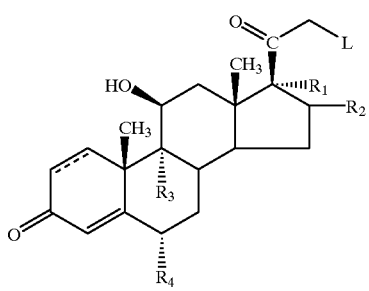

(II)

wherein $R_1$, $R_2$, $R_3$, $R_4$ and ═ are defined in claim 1 and L represents an appropriate leaving group or L represents a halogen with a compound of formula III

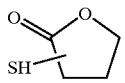

(III)

and salts thereof;

B. reacting a compound of formula (IV)

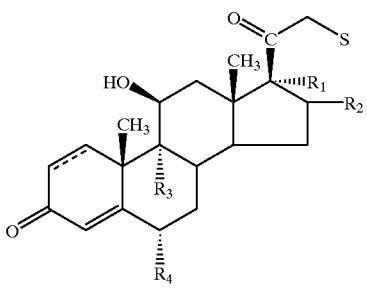

(IV)

and salts thereof, with a compound of formula (V) or formula (VI)

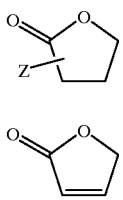

(V)

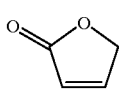

(VI)

wherein Z represents a leaving group.

* * * * *

UNITED STATES PATENT AND TRADEMARK OFFICE
CERTIFICATE OF CORRECTION

PATENT NO. : 6,013,244
DATED : January 11, 2000
INVENTOR(S) : Biggadike et al.

It is certified that error appears in the above-identified patent and that said Letters Patent is hereby corrected as shown below:

On the title page, Item [57] and claim 1, delete the formula:

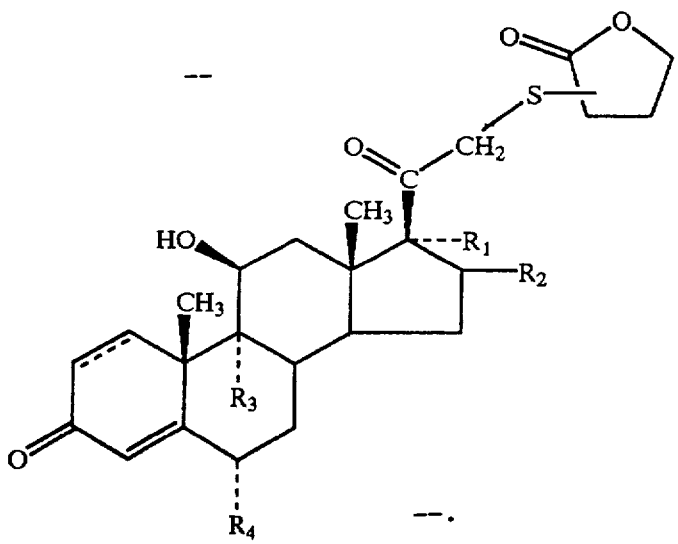

Signed and Sealed this

Thirteenth Day of February, 2001

Attest:

NICHOLAS P. GODICI

Attesting Officer

Acting Director of the United States Patent and Trademark Office